United States Patent
Yoon et al.

(10) Patent No.: US 12,280,081 B2
(45) Date of Patent: Apr. 22, 2025

(54) **COMPOSITIONS AND METHODS FOR INHIBITING THE PROLIFERATION OF ENTEROTOXIGENIC *BACTEROIDES FRAGILIS***

(71) Applicant: iNtRON Biotechnology, Inc., Gyeonggi-do (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Eun Kyoung Oh, Gyeonggi-do (KR); Geun Woo Lee, Gyeonggi-do (KR); Soo Youn Jun, Seoul (KR); Sang Hyeon Kang, Seoul (KR)

(73) Assignee: iNtRON Biotechnology, Inc., Gyeonggi-do (KR)

( * ) Notice: Subject to any disclaimer, the term of this patent is extended or adjusted under 35 U.S.C. 154(b) by 0 days.

(21) Appl. No.: 18/498,455

(22) Filed: Oct. 31, 2023

(65) Prior Publication Data

US 2024/0050500 A1   Feb. 15, 2024

Related U.S. Application Data

(63) Continuation of application No. 17/227,287, filed on Apr. 10, 2021, now abandoned.

(51) Int. Cl.
*A61K 35/76* (2015.01)
*A61P 31/04* (2006.01)

(52) U.S. Cl.
CPC .............. *A61K 35/76* (2013.01); *A61P 31/04* (2018.01)

(58) Field of Classification Search
None
See application file for complete search history.

(56) References Cited

FOREIGN PATENT DOCUMENTS

WO   WO-2014070225 A1 * 5/2014 ............ A61K 35/742

OTHER PUBLICATIONS

Tariq, M.A et al. 2020. Genome characterization of a novel wastewater Bacteroides fragilis bacteriophage (vB_BfrS_23) and its host GB124. Frontiers in Microbiology 11: 1-12 plus Supplementary data; specif. pp. 1, 4, 10 (Year: 2020).*
NCBI Blast sequence search. Seq Id No. 1. Datasheet [online]. Retrieved on Aug. 5, 2024. Downloaded from the internet: <https://www.ncbi.nlm.nih.gov/nucleotide/MT630433.1?report=genbank&log$=nucltop&blast_rank=25&RID=B2J36WS3013> pp. 1-4 (Year: 2024).*
NCBI ORFinder. Open Reading Frame Finder. Seq ID No. 1. Retrieved on Dec. 27, 2022. Downloaded from the internet: <https://www.ncbi.nlm.nih.gov/orffinder/> pp. 1-2.
NCBI Blast. Nucleotide sequence search. Seq ID No. 1. Retrieved on Dec. 27, 2022. Downloaded from the internet: <https://blast.ncbi.nlm.nih.gov/Blast.cgi#sort_mark> pp. 1-3.
Zaczek-Moczydlowska, M.A. et al. 2020. Genomic characterization, formulation and efficacy in planta of a Siphoviridae and Podoviridae protection cocktail against the bacterial pathogens *Pectobacterium* spp. Viruses 12(150): 1-16; specif. pg. 2.

* cited by examiner

*Primary Examiner* — Adam Weidner
*Assistant Examiner* — Sharon M. Papciak
(74) *Attorney, Agent, or Firm* — SIMI Law Group, PC

(57) ABSTRACT

A composition for preventing or treating an infection or disease caused by enterotoxigenic *Bacteroides fragilis* includes a Siphoviridae bacteriophage (Bac-FRP-5) having an ability to lyse the enterotoxigenic *Bacteroides fragilis* cells and a pharmaceutically acceptable carrier. A method for preventing or treating an infection or disease caused by enterotoxigenic *Bacteroides fragilis* includes administering to a subject a Siphoviridae bacteriophage and lysing the enterotoxigenic *Bacteroides fragilis* cells by the Siphoviridae bacteriophage.

5 Claims, 4 Drawing Sheets

Specification includes a Sequence Listing.

SEQUENCE LISTING

```
Sequence total quantity: 1
SEQ ID NO: 1          moltype = DNA  length = 46506
FEATURE               Location/Qualifiers
misc_feature          1..46506
                      note = Siphoviridae bacteriophage
source                1..46506
                      mol_type = unassigned DNA
                      organism = unidentified
SEQUENCE: 1
ggtgagtatt atattctggt tcgacacccg gacaattcca ggtgctgaag ggtataacgt 60
tgagttcgtc aagcaacgta tattacgagc gttaacgcat gaacttgaat tgtcatacgg 120
aggtttgaac gttaagcgga tatttaatga cgcaaagaat gtgtatgacg gttttagcat 180
agacaagacc gacaatcaat tctacgtata tccttatgct tgtctaaggc ttgtatgtga 240
catggtagca ccggaggcgt gttatccata atacgataag gggaatatat atatgtatat 300
atcccctttt gtgttaaata agtgttaaag attaaagttt tgctttatgt ttcaaatatg 360
aatactatct ttgttgtgtc gaaagagata gagtagtaac aataaaaat gaaagatatg 420
acagcaacag aagtaaaatc agtattagca gataacagaa atttagttat tagctttttt 480
aatgaaaatg ttaagcaaga taattttttat accttatctt ggtttatgac aaggatactt 540
ttggaggcta ccgcatcatg gggaagaaga aagaacgtat ctgaaaaaga agttatgcag 600
gttatcggta aggttatgcg tacttacccc caaatagcaa aaggacacgt tagcaactat 660
caaaaagcag ttaaatactt cggtgcagaa cttgcaaatc aaatatctaa tgcaagatag 720
ttaaattcat gttaaatatt aaagtttttgc tttgcatttt aaaagttatg cttatatttg 780
caatgtcaaa caacgaaaga ccccacaatc taaccaagac gcaaaaagat tgttgaaaga 840
tcaagttcgt aagcgtagaa aataagcaac ggtatctaca aagggttaaa tgaaggttcg 900
gtatccgatt aaatgaagct ataaagccta aatctttcga tgaatgacaa agtagtaaca 960
attaaaaaac aacaattatg aaaaaagatt tatttattca gagaacagtt gaaaaattta 1020
ttatgattga atttgttaag ggcaacatgg atactaaaga gcaggtagat agtatgatag 1080
aattagttca aagaaaatta gacttttcat ataacgaagc atgtgacttt ataaagaatg 1140
ctatcggtat aaacgcttaa attaaaatat taacaagtgg gggtaatacc ccacatttaa 1200
aataaaaata aaatgaacga attaatttct attagagaaa acaaagggaa acaagttgtt 1260
tcagcacgtg aattgtactt atcgcttggt tacgatagta gtaactattc aaggtgggta 1320
aagtctaata taattgaaaa tccttattct attgaaggtg aagattgggc cccactcgtc 1380
acaaatgacg agcctattaa tcagaacgtt aacccaacaa aagattatgc aataacaata 1440
gttatggcta aaaaaatagc aatgatgtct aaaacagaga taggaaataa aattagggac 1500
tattttatcg aatgtgaaaa gaagtcacaa ctttatatac ctaaaactta ttcagaggct 1560
ttaatgttag cagctaaaca agcggaagaa atagagaatc agcaaaagca gattacaagc 1620
atgaagccca aagccgaata tttcgatgaa gtgatagatc ggaacggact aacaaatttc 1680
agagatacag caaagctgtt aggcgtgtat gaaaaagcac ttatctttct tttgattgac 1740
aagaagtaca tataccgaga tcagaaagga aagttgaagc caattgccaa gtatgttgga 1800
gactatttag agttgaaaga atgggcaaaa ggtgaaaaga cagggaccca aacactggta 1860
actgcaatag gtagagatca tttttttaaaa ttaattaata acgtaaaatt gtaataacat 1920
ggagaagcgt agactatcta tatcagacaa aggtatgttt attccggaag aaggggaaat 1980
attttttgcg gaagtaccaa ataagggat agatcgaaaa gtgaaaacat tggtgtctaa 2040
agataggaa gcatgtgaga agtgctgttt tcgtagtggt gaattaggct ttttgtgtcg 2100
gggagtacgt tgcataacaa tagacaatga aacacaacta acatttagga gggtatcaga 2160
tgggaaaatt taaaagcgta gaactgtatg acaccttcac aatagatcac ccagtgacag 2220
gggaaacgat cagagcgcaa gcaatggaag gtaacaatgt aatatcatgc agagaatgcc 2280
tatttagaca aaaggagttt aaaaagatat gcccgcttat gcgatgcgtc gatatggcta 2340
cgggaaagtg tcaaacctat aaacaagtga agttatgaaa agattagatt catcatgcct 2400
accaataaat ttggaggtag gcgaaacaat ggagttgata gataaagacg gtaagtatca 2460
cctattgaag tgtgttacat cagatgaaaa tagttcgtgt gaagggtgct tctttactaa 2520
```

```
acgaaatata ccctttaact gtgattctgt aatgtgctca ggactggaaa gaggcgtgaa    2580
aagaggtgat gtgatataca tagaacttcc ggtaaaggac gaatttaagc aagacgaaga    2640
aagcaaagat gatatttatt acgaggaatt aacttaaatc aatggttact tttggtaagt    2700
atagtactta cttttagtaa ctgttaaagc gaaagtttaa aaattaaagt tttaatataa    2760
tagtgttgac ttatgaaaga agaagttatt ttaatgctct cagagctacg ttctcaaatc    2820
aatgacacaa ttatgcgtgt caagaaagaa agttccgcag atggcaagaa aatggtgtct    2880
atgttgatgt cttgcgactt cgttgatgtg tacgacttgt tggtaggaga aacgagcgca    2940
tttttggagt atctggaaag ttgtggttc atcagaacgg aaatgaaaaa gattaatgtt     3000
aatagcaacc gttcttatat tcagatgaa agggtgtcta ttcacgaatg ggtaagttt      3060
gtgaagggta aggggtgttt gtgtcaccct gcattgattg ctttgtatag gaactataca    3120
gaaaatagct aatcatgaat tattaagtaa ggaataggag gttagcgcct cctttcttg     3180
tttatataca tttgctttt atccgccctc ggagagattt agactaatgt tttaattatc     3240
aattgatttt gttttcgct atttattcat acatttgtac aaaactaata tgttagaata     3300
tggaaaaagt aaatttacta ttaaattgtg cgctgttggt ggcgtttatg gcggcttttg    3360
tcgttggttt attgcgaaag tggggagtaa tcgaaagatt gcaggtattc ggtgatatgt    3420
ggcttaaaaa gctattccct gcatatagtc gtagtttcat gtatcagttg gcaggctgca    3480
acttctgcct gtcgttttgg gcttcgtttg tgttatctat gatgttcgct attacattcg    3540
gtgagccgct attcctcgct acaccgttat ttgctgcgcc tgtttgtcga atcttaattt    3600
aatcagtatg aagtataata gcgtattacc accgttgcc acggttgaga ttatcccgta     3660
tgatggcata gagtctttgc gaagtcttac cgataaagtt gatatgcttt cagagtctga    3720
aaacatggga gtatacgaat tgggcgaaag aattatgaaa tgttataaag gtgattttct    3780
gattaaagaa gcaaacgggc gtatctattg cctcgactct gatgcgacgt caattctatt    3840
tgagaaagga ggtgaggaat gaaagtagga cggcatgaag ttgagttgta cgaagggata    3900
gactcactac ctattgcgag gtatcaaaag ttcaatcggt tgatgttggt tgattccggt    3960
gtaggctcta ctattgagga attggatacc catctgaaac gggctattct gtactgcaag    4020
actaacccat atcacacgta caccgaacta ttaaaacctg acgtcgtt caacatggct      4080
atgaatggta ttcaccctgg catgattgct ttccggtgcgt tcgttaagtc gttggacgag    4140
aaggagtatc cggtacacat aacgacgag caattgcagg aaatacacac cattctatca     4200
gatgtaaccg tttcggagct atcagaggca aacgaggcgg tcaaaaaaa aatagagggt     4260
gagatgtcgg tgtacttccc ttcattgagc gatagccctc agatcaagga gtactacgat    4320
ctgaaattgc agctactaac cgcaatgtta gatcaaacag cgaacgggac ggatagaggt    4380
gaggaaattc agtcattgac cgatcaactg acggtctact acccgcctcg ctgctttcaa    4440
ggtgagaagt cagtggagat acagtcggat aaggagtttg cggagatgtg cctgctaatc    4500
acaaaggaga tgcacctcaa tgcaaaggac atgaccgtat ttgatttcta ctcagcattc    4560
gagatgatta aaagacaaag taaaaaagct aaaaagtaaa ttatatggca aacgatgtta    4620
aaggaataaa atatagcgat ctgatacagc cagataacag catatcggag gcggtcaagc    4680
agttggagca actgcaaaag ctatatgaaa cgatgttaaa gcgtatcgag aaggtgcga     4740
agggactgca aaagcctcta agcgagggag gcggagcgac ggaggaagga cgaaaaaaga    4800
ttgatgctta tgaaaagcag gtgagatcac tggcacgtgc tgaactttgat ttgaagttgg    4860
caatgacgga taccgctaag gagatagccg tattgaagca gcagcagacg gaccaaacac    4920
gcctcaataa gttagtagct aaacttaata actcaatggc gggtagctac aatgccctgt    4980
ccgcacaata cgagctaaac aagattaaga tgaacaatgc ttcgcagtcg tatctagaga    5040
atacagagc tggaaagaga cttgttaagc aaacagctga gatatacgca gcgatggata    5100
agtatcaaaa gagcaccgga aaacacactc tcagcgtggg taattacaag caagcgtttg    5160
acggtttagg tttctcagtg tcacaggttg cacgggagtt gccatcactc gccatcagtg    5220
caaataccct cttcctagct atctctaata acgttccgat ggtgatagac gagatacaaa    5280
aactgagggc tgcaaatgaa gcgccgcaa aagcaggtca caagta agtataaccg          5340
ggaaacttat taaggcgatg ttttcgttta acacagttat ggtacttgtg cttactgcat    5400
tctcgatttg gggtaaggat ataataaact ggataggaag cttattcacc ggaaagaaaa    5460
gggtagataa cttgacaagc agcccttaaac acatggtaga cgctatgcaa aacgcacgct    5520
tagacagc gaaagagact ttaaaactca acttgctgta caaaacagct acaaacaaag    5580
ctaaatctac aaccgaaagg acgaaagcgg ttaaggcatt gaaaaaggag tatcccgaat    5640
actttaaaaa cctaagcgat gaagaaataa agttagggaa agcgtctaaa gcatataaag    5700
aagcaactaa ggctattaca gaaaatgcaa aagcacgtgc cgcactggat aagattacag    5760
agttgcaaaa ggagtatatc gaattagacc aaaaacgtat cggcgtgttg acgaagcaag    5820
tgcaggcaca aggagaactt gcaaaagcgg agaagtacac cgcaaaggta tcgtctacca    5880
taacagcaac gtctacacag gcagcgagtc aatattatgc agcgacggca agcaatgtta    5940
ataaactcaa agatgatatt aaggagtacg gagatgaagc tgaaagaca gccttaaggc    6000
aaaaggtact agctaaatca atggaaaacc ttactaagta tgttaccgtt gattctctga    6060
ctggtaagga cacaaatacg gatagcaaaa agaaagatt cgacttacta aaagcctacg    6120
aggaaagcag agtagctctg attacagact cccgaaagaa agaagaagcg gagataagag    6180
aggcagctag ggcggaactt gctaagttgg agaaggacac aacggagaag caagagcca    6240
cacagcagta tgcagatacc gtttataaca tagaggcaaa actgcgtagg gacttggaaa    6300
agttgcgtga aaaatgggac ttagaggact tgcagaaagc acatgacttt atgaacgaac    6360
gtctgagggc tgtgcgtgcc ggaactggtg aagaactatt acttcaaaca tccttcttg     6420
agaacgagcg caaacaggac gaactgaaaa ttaagcagtc aacggacacc gaggctgtaa    6480
agaacgagcg tcttttgata ttgcagcgtg cgtatcaatt ggcgtctatc aagctacggg    6540
aggacttcac gaaggatcag aataatcgta taatatcccg gtctgtgttc cgcttgcagc    6600
aagaacaaca agcgagtgaa tccgaattta acattgtgca gcgatcggca aaagagcaag    6660
aagttttccg gttgaatgca gagcggcaga aatgggaaca aatattagag ctaaacgat     6720
tgtacgggtc tcagattaca ggatacgagg ttaaaacggt tgaggacact atcgcaggta    6780
tagataatgc catcaagcaa aaagcgtccg gttgggattc tgaacaaggt gtatttggta    6840
acctgtttga tctgatgttc ggaggtgcgt tcggtgacaa gggcggaaag tccggcaaag    6900
agcgttcaga ggaatttaag cagtcgattg cagacgcttc agcagtacgg atagaaatc     6960
ttaagagcgt agcacaggca agggttgaag cggcagaaaa ggccgtgcaa gctgccgaaa    7020
aggaagtatc agcagacaa aaggtgttag acgctgagat acaagcgagg gcgaacgggt     7080
atgccaacaa cgtagcaact gcacaaaagg aactggactt tgcacgcaaa cagcaagaga    7140
aagctctgag ggataagaag aaagcacaga aacagcagga acgcatagat acgcttatgc    7200
aggcaagttc tttggtgact gcgaccgcta acctgtggaa agatttagga cttgctgcta    7260
```

```
ttcctgcaat tgctcttatg tggggctctt ttgcttttgc taagatcaaa gcctctcagt  7320
tatctaaagc ctcagaccaa acggaggaat acggtgacgg tacggtagaa atgattgatt  7380
acggaggctc acatgcttcg ggcaatgacg ttgatttagg cacaacaaag gacggtaaac  7440
gcaggcgggt agagcgtggt gaatatttcg ctgtaattaa caaacgttca tctcaacgtt  7500
atagacgctt agttccggac ttgattaatt cactgaataa aggtacttt gaacagaaat   7560
atctaaacgc ctattccggt gctgatgaag tcacgaacat tatgcagggc ggaaacgtag  7620
atttgtctaa tgtcgaacgt gatttgaagt ctatcaagga gagtgccgga cacaagttta  7680
taaccggagc tgacggtaca atcattgaag tgaaaggaaa tgttaaacgt ataatcaaaa  7740
cgaaatgaat gtaaaggact tgaggtttaa aatcggggt gtaattgtac accctcttta   7800
caccgagcta aaacggaagt tcggcaaaga gaatcaacag gagtttttca gagagacaat  7860
agaaggtagt ttaactttca tcggtgcgga ctatttgtta ataaagaata agagcattga  7920
ggatgttatc tacatgacta tcgaacaaaa ggacaaagga cagacggagg cgcaatatac  7980
tgtcatttat gaagccatt tcagtaagac tgattgcgag atagataacg acaatcggag   8040
ttgcaaggtt aagttatcac ctaaagacgc ttattccgac acactccgtg acattgagaa  8100
taagtatgac ttaattaaac tatcgcctgc attaacgcag atcggagtgt ataaacgtcc  8160
acttgttcag gtgtatattg cgggcgccgg aacaatatct aactaccttg caggaactca  8220
gtatgaaact gatgtgtata acgtagttac ggatagtaaa gagcttactg acaaacacta  8280
ctttgcttc tttgctgcat ataatgaagt agaagttaag gcagttccat atcaatcttt   8340
taacggcaaa tactacgaaa agaacggtgt atacacgaag ttggacggga attactcaat  8400
taaatggagt tatagcgagg gtcttaatat cggttatcta tcacttgaaa atagggacgg  8460
tgtaatactg tacagatcgc aaaaaatcac atggaaggat aagagctatt tctacataga  8520
tgttctgaa attacgtttg aaagggtagt aacgaacact acactccctc agtccttcgg  8580
tggaaactcg gtattgcttc aaaaggtatt tcaacggttg ctgttagacc ttcctgagtt  8640
tgacggtaaa ccaacaggga gattatcttc cgaagatgtt tacccgacaa atagtaatta  8700
cctgtatgcc gcacctcttg tgggaaacta tttctatacg tctactaagg tgcaggatgt  8760
tcccaccgaa tatggcgtaa acgatgaagg aaaatacttt gttgataact ttctccctgc  8820
cgttgttgga gcgggtaaac tgtatccggt gtgtcggtca aggtggggga atatgtctat  8880
atggttcgag tacgatttag ggtatagcgc actggaagaa cgcgcccgaa agaagtacat  8940
tcttaagcac tccttgcca tcagtgacgt aataaagacg ctactcacac aggtagaccc   9000
aacgttgcac cacgaagcca cagaggaata ttcacgtttc ttatacggta cgtctaatcc   9060
gttgactggc gcaccttaca gagtgtttat cactccaaag agtaacattc taaagggtga   9120
atacgatcag cccgctaaga aggcagaaac gacactcagc gacatattta aaatgcttcg   9180
tgacacaatg agactgtact ggtttataga cggtgataaa ctgaggatag agcatatatc   9240
atacttcatg tctggaggct cttatactgg tactggtacg gtcggcatag acttaactaa   9300
gttgaggtat gcaaagagtg ggcaactatt cacgtttaag accaacacgc ttaagtatga   9360
taaaacagac ctgccgtcac gctttgaatt ttccttggatg gacgcacacaa cgaatacctt   9420
cgcaggcttc cctattgatg ttaaatcaaa ctatgtgcag gaagggaaga aagaggatat   9480
tagagtagct aactttttcct cagacgtgga ctacatgctg ctatccacctg gtgacttttc   9540
ctcagatggt tttgcgctgt taggtgcggt tcaaaagtca ggcaaatggg aattaccttt   9600
tgttactgtg ccgctgacgg ataaatcggg taacaactac accgttacgc ctcaaaacgg   9660
ttacatgtca ttcctacacc tcgtgaagta ctacatgtac gatatgccag ccgcaaacat   9720
tgagcacgaa ggagataaaa cggtgaccgt acaacgctg aggcgaagta tgacacaaga    9780
cttatcattc acctatgaca caacgcccga tccgatcaag ctaatgacta cggacgtcgg   9840
aaatgggaag cctctaacca tgactgagga cttaacaact cgtgaaataa ccgtttcact   9900
cacatatacc ccctcttaat gggggtattt ttgtatattt gcccaataat caaattttta   9960
taaatatgaa tacattcaac aactttagtc cgttagcttt cagaaagaaa agtcagaaag  10020
ctacgtataa aaaatggtac gcctatggta aggagttcgc tttgccgttt agtacaaccg  10080
aattgccacc gtttcagttt acggttacca atcttccatc atttgaccct actacgtag   10140
aggtgttct tgtgaatgaa gctaccgaag cgagaatcgg aacgggtatc aaaataaaag   10200
ttgatacgat ggacgaacat aactcagttt tatacgtatc accagggagc aatgtgtatg   10260
ctaaatcagt agagccgggt gtatatcgtg ctgagtttac tacccgaa ggtgaaacat     10320
acatatccac gcctatttgc gtgactgatg gaattgaaac taataccaac tttgttaaat   10380
tggagtactg gaatgatgaa aagttagctt atcctaatgg cttcgttacc actggtacgg   10440
ataatgattt caagtttcag atgtatatcc cgactacctt ctttaagccg aaatacgagt   10500
ttgaggaaga gataacaaag agagcggct ataagttttct cgaattgcag acttgcaaca   10560
aggtgttcgg ctttagtttc ctcgcacctg agtatatctg tgacgctctg agactggtgc   10620
gtctgtctga ctatatccgt ttcgcccatg acggtgagta ttacaacgct ctgaacttcg   10680
agtacaatcc ggactggcag gataacggat acttggctgc tatcgaatgc caattttgaaa  10740
cagacacaat catacaaaaa ctcccttctt tcaatcggag agatagagag tcttttttata  10800
atgccctact ggcggatatt gaaactccaa ttctgttttag tccggacaca gtagggctgt  10860
attaccgtga atttaaacag ggagagccga caatcaaagg taagtaatc cgggaactat    10920
cacctattga cttgatagac gaaaatacta ctattgccgt ggatatgggt gctggtgagg   10980
cgcgtaaatt caacccttta cgcatgttag aggggtacat ctcgaagaat cacgaagatg   11040
taacgaaatt ccttttgtcc cttcgtgagg gcgtgaatat cggtacacct aatacaagcg   11100
gtgagtatcc tgcaagcgta gacaggggacg ggaacactaa gttaaaggac atacaggga    11160
atgatgcaac gttgaacaac gtcacaggaa aagatgctac gtttaaaact gtggaaactg   11220
gtttcttaac tgttaacaag actgccgcaa caattgacgg aatgggtaat gccaatgtaa   11280
acgatttaac tgcaagaggt gactctaagt tgcgcagcga cgtatataca gggcaaaaa    11340
atggcagcca taccggaaag ataacgaaag aaggacagtt gcagtacctt tcagctatca   11400
tctacgagtt cctttcgtcc gaaacgttcg ttcctggctt cttaggtgaa ggatttaaaa   11460
tatggttgga aagcggtaac tggcatatcg aatgcgataa cctaaccgtc cgccaaacta   11520
tgaacatctt tgagttgctt atccaaagaa tacgtagcgt caacgagct attgttgtat    11580
cccaatcaaa cggtaaattg tcatccgttg aagaagtagg aacacaatac aagctaacca   11640
caggcgatga atttcccact tttcaagagg gcgatttggt ccggtgccag acgtttgcag   11700
gctatcaagg tgcggatttt acttttgact ttactcagtt tgcaaaatat gactattccg   11760
gtggtgcttt tgatagcagc ttgattgatg ttacacccga ctctattagc tttaacttga   11820
atgatactgt taattccggt tttgcattct ataaatttc agagtcaagc cctacaccaa    11880
ttgaaatacc ttcatttacc ttgactttgg agggaggcta tcctggtatg atggcttttg   11940
ctgccggact tgattcaaat gacagtccgg tagagggtgt aggcgtattg cttcaaaacg  12000
```

```
gtgataatgt tattccggct attaaagcag cgcaagacat acacaacttt gctataacaa   12060
taactggtga ttccggtcac ggtgatggta aagttacagt aaagcaaaag aaagcggcag   12120
gaagcgcacc aaacaatagc ttagttaaat tctattgggt ggaagttaaa tcggttgacg   12180
gggcttcttt ctttgcagat aaagcggagt tcaacggtgt tgttccggct gtcggtgacg   12240
aagttgtgca gatgggtaac acgaagaact cagaaagaca ggcattaata tacatcacag   12300
cgcaggaaag cggcaagccg tacattgaga ttctgaacgg tgtcaaggca aagagcctaa   12360
ccggaaccga tcgtacccgt ttgggcgatt tgtctaacat tgtagacccc gatttcacag   12420
gtgatgcggc cgtgaaagga actggtttct attctacgaa tgctttctta aaaggtatct   12480
ttgtacttcg taacggaaag cgtgtagagg acgaaattaa gatcgcaaag gacgcagccg   12540
atcaagcagc acaggacgca gcgaacgcag cacaatcggc acaggaggcg aaagatagac   12600
ttaacaaatg ggctgatgat ggctttatct caccgactga gaaacctgca ttgattgacg   12660
aaggaaagcg cattcaagcc gagtatctgc aaattaaagc gaatgcggac aaatacggta   12720
ttcttgtaac tgaatacaca gaggcgtata acaactatct gaacgaactca cgctatcact   12780
cggccgctac accggaagat attgccgtgc gtccggaact ggcacagagt caaacggctt   12840
actacgacaa acgcaacgga gcgttgaatg ccattgcgga cgctgctaaa tcgtatgtag   12900
atgaagcgga taagaagcta aaggaatact tagatactga gataactgct attcccggta   12960
agattgaact cgctgtgcgt agtttaaagg tggctgatgt taacttattg aaaggttcat   13020
attatgagct gaaaaatgat gcctataacg tggggtatta ccattatgat gtaccagcta   13080
tagacgaaaa ggagtacact ttaaccgtat gttacacact tggaagcagc aatacagaaa   13140
taatagcata ctctaatggt ggcgtaagtc gtattgctac ccttggaaca aaaggagata   13200
aagttgtaga aagttataag attactatgg caggttataa accgagtgaa ggtatgtatt   13260
tctttcaatt cccaaacggt acatacgggtt ctaaagtaca ttgggctgtt ttgactgatg   13320
gaaatttggg tgtaaccagt tggataccgt ctgcaagcga aaagaatgta ggacttagaa   13380
acctatgttc gtttaagcgt atcactgatg ctggctttac tttcgcctca gattatcaag   13440
atgacgaac attttttcatt gatttaccta aacttgcttc cgagagttat caaagttcac   13500
aaaaagatat gtttggtctg acttatata gtattatata ttttgtgata   13560
catttagtta tataacaccg ccagatacag ataaaaaagg tacgttaact atatatgtat   13620
attatactga tggtacacat gatttagctg tttatttggg tcgagataga gcgtttaaca   13680
actgttttcac tacaaacaaa cctgttaaag ctattgttgg tacttatgga tatggttttc   13740
acccacgtgt cagacttggt gtgtacgaaa caaattttccc tgtgtcttgg agtccagcac   13800
ccgaagatca attgtatcaa tcggttaaat acactgatac ccaaatcttg gcggtagatg   13860
gaaagattgc attatctgtt aaaactcagt tagagaaatc tactatcgga ggtaacaatt   13920
tattagacgg gtcaaaggt tattggttta atgaatcaga ttatttatca aatgtcgagt   13980
tggtgcgtga tggtgacgct ggaataactc gtattaaggg aaacgggttt ttcaattcat   14040
ataaaagatg gatgccagtt gataacgtaa tggtaaggaa tacaccgtag   14100
gtatagatat aaacgttcaa ggaaattatt ataatgacga ttattttttgg gtaaatatac   14160
gtaggtatga agattctcag gagataatgt tagcacatga acaggtttat attgaaaata   14220
aacccaattg ggtaaggtat tacgttactg ttaaaactcc cgatagcggt aatccgaacg   14280
attggctatt cctttgtggt ttttccggta agaacgaaac gaataatgta ggtgtgagtt   14340
attattatag aaatataaat atgactgatg gaagtatcgg tgcttcgtgg agtccatctg   14400
ccaacgacac ctacaacaaa agcgttgaat atacaactca gcaaataagc attgttgagg   14460
gtaaaatatc acttgaagtc agcaaagaga tacaaaatac tcaattcgga ggtaacaact   14520
tgtatagcta cacgagttca ccgcttaatc agatgagtcc tgagccaatg actgtaataa   14580
ggcttataag tgaacacgga tttcgttgg tgggtggaaa aggcggtcag tcccatgtaa   14640
gaatacctaa tattataccg cctatccccg gaaggtatac tgtttccgga tggataaaag   14700
ggtctcaaag tacaacgcct ggtataacta ttgatgtatg cgattctgaa aggattcgta   14760
taaccgctac tgctgacaat aattggagtt attttaagca cacttttgat gtaagcaaaa   14820
atgcaagttc accggaagtg tataattttt tgatataga agaaatatca tgggcttata   14880
tatgggtgaa agatttcaaa gtagagtttg gcgaagtcgc aaccgcatgg agtcccaacg   14940
aacaagaccc agtatataaa tcggctgagt acacaaacag taagattgac gtaacaaatc   15000
agtctattac agcagcagta cagcgaataa acgcaaccga aacaggtta acgagtgcta   15060
aacttaaact aactgatacg agcgcaaaac tatccgttgt tgaaggtaaa gcggatggcg   15120
cacagtcaac cgccaatagt gccaacagcg cagcaggcgc agcacagtct actgcaaacg   15180
ctgcaaattc attggcaggc actgccaaca ataaagcgga cgcaacaaat aacgtttttgg   15240
tcaagactgg aataaacatc acgtcccgca aaatcgtact aaagtctgat aacgtcctct   15300
ttcagaataa cgcaggacag caaacgcgag cactgaacgg caacggtcgg ttgagtgcca   15360
acgtgattga ggcgggtgag gttgttgcga atggctttgc tgcacagcga ataacaaccg   15420
gaaacttgac tgtgacagat ggtgcggtga ttgcgggaat gactatttct ggaggtgtcc   15480
taactggtaa gaatattaat attacagatg gcgcaaaagt aggtagtttt actatctcga   15540
gcggtatatt ttccgcacaa gaagttccgg caggataca aatgactcta gcgggcaatg   15600
ccgctacttt tgatagtagt ggagtacgcg tagagaataa ttcgggcagc tatgcgttga   15660
ctactacggg caaaggaaaa atattcttaa caggttcgga ttttttgggtc cagtgtaagg   15720
acgttgattt tatgggtgct caaacatgga aagccccagg tgtttttttac gcatgtacga   15780
ttttgggaaa cggagcaatt ggtaaaacat ggggaaacca tgacttttcac ataacaaggg   15840
taattaaaaa ctcaacaggg agatatactg tttatacgac tggttcgaat ggagattact   15900
ttgttatgat tacagcgtat aatgttactt catggctcag tacaacagta gaaccatact   15960
ccgaagggca gtttacgtac aaagtattcg atgtaaataa tggcatgact gacagcgcag   16020
ttattattta tttttgtggc atggttaggt agtttagtgt tttaattgac ggtaagttgg   16080
ttttatcctt cttaccgttt acctttgtag caaataatt attcattcac aattaaatat   16140
caatttttat ggcaacaaaa gaagctattt ttagtttgga gagtgttaag tactcgaaag   16200
aaacacagat tttggattat agttttgaga ctgataacgg actttttaaaa ggtcagatta   16260
caatcgtaca gcaacccgat caagtaaagc agatcacaca ctgtacagct gaggtatcag   16320
ttaaagaaat ggttcaagtg ccgggaacgg ataacacgcc taccatgcag gaacaatatg   16380
ttaagtgggg cacttttgcg atgtcgcagg ttcgtttttg acttaatcaa ttccctgtac   16440
acgaaaagac acccgctttg ttgggagatt ttcagaacta catttttgca ttaactaaac   16500
aatcagaata atgtcacagg aacaaattag gctgctgatg gtatccacat gcagccctat   16560
tcttgcattt ttaaccccta cgtccggatt cttgacggca cttgtgttta tgtttgtctt   16620
taacataatt tgcggtatgc gtgcggacgg tgtaagcgtg tcaattagag gagctcaaag   16680
attcactatc tttaaattcg tatcggcttt acaggagttt ttgctgtata tgatgattat   16740
```

```
agtagtgata ttctcggcag ttacaaagat gggagacaaa gacgctgcaa tcatgtgcgc   16800
aaagacaatc acgtatgtgt ttatgtacgt ctatttatgc aacggtttcc gtaacttgtg   16860
catgacatac ccgaacaaca aaggtttcaa gctgatctat cacattatta gatttgagtt   16920
taagaggctg atgggtgaac atgcgtcaaa gataatcgaa gagcaagaag agaaagaaaa   16980
acaggttatt cacaagggg tataatgccc cctttaaaca tttagattat gaagtatttt    17040
acgattaaag aacttacaaa gtcctctacg gctgaggcta aggggataga taacacccca   17100
acacaggagg ttgagcgtaa tttaacggct ttggttgaaa acggtattaga ccccttgaga   17160
gagatttacg gtaaacctat aacggtcaat tcgggctatc ggtgcccgga gctaaacagg   17220
gctgtcggag gcgtatctaa cagccaccat gttaagggat atgctgctga tattacgagg   17280
ggtagtccgg aagaaaacga acggttgttt aatatcattc ggcacaactt taaattcact   17340
cagaatttag atgaaaaagg tttccgatgg gtgcatgtgt cttacatccc atctgatttg   17400
cgttgtgagt cacttcattt aaaataaaac agtatgaaag ctaaataac agccatagta    17460
gcattttctt tcctttgcct actaattgta taccttctta ggtataacgc gaaactgagg   17520
gaagaaaacg gcattctgaa caggaatgta agtgtactta ctactcagaa tgtagcatac   17580
cgaacggagt ccggcaaatc agcaatgaaa gcggaggaac taaacctcgc cttgcgtcaa   17640
taccggaaca cattgcaggg gaaagacggc actataaagg acttgaaaca aagtatcaaa   17700
gacttaaaca gtcatacaag cattcaaacg tcaacggaga gcgtatttc cggctctcta    17760
cgtgatagta ttataattcg tgatagtttg gttgctgaca cattaaaatg cttgaatttc   17820
gcctctaaat gggtaaatgt taaaggatgc atagaatcgc ccgatgtatt tgcgggcaag   17880
gtaaccgttc gggatagctt agagtattg aacatagaac accggaagcg tttcttatgg    17940
tggagattaa agaaggtgaa gtataggag tttattgtaa ccagtaaaaa cccagatacg     18000
caaatacttg atttaaaggt gactacaata attaaatagt taacgttggt taaagctatt   18060
gcaggtataa aaataatgcc tacatttgca ctcagagaat tacaaataaa taaattatta   18120
atcatttctt tattggtaag tctttatgta gaagcaaacg tatcattaac aaagcgttgt   18180
taataattgc aatcatggtt aatattaagt gattattccc tactggtttg tgaaaatagg   18240
taggtttta aaaagagatt tctattcata aatatataat ataggttaat tagttaggta    18300
attgttgttt attggatttt ttgtcatttt tcattttcc ccgttgcttg tgaaagtagc    18360
gggttttt attgtcttgt ctcagatgtg caaacgttaa ataagtgtta aagattaaag    18420
ttttgatttg caattaaag ttttgcttta tatttgcagt gtcgaaagaa acaaagtagt    18480
aacattaaaa tatacgatta tgaaatttaa aacatgtatt tttagagata ctcttaaaaa   18540
agagtgtttt tcagtagagg ctaaatcaat tagaggcgca ttgactcaga ttaagaaaaa   18600
gcagcgtgaa tgcgctgaaa agttcgggca tacggtattt tggactatct ttgaaaacga   18660
aatgccgac tcaaatatgc gctgcatatt ggtaacgtat gtgtttccca atggagatat    18720
taaacaagat gtattataag caaattgaat cattatgaaa ttcataaaga agcaaagtga   18780
taagatactg atagccacaa gggacgaagc gtttgatgta tacgtccgca gtcacccagt   18840
tataagtagg cttattaggg agatcgggat agaaattatt cagcaagcgt actacgcaa    18900
tcatatagcc cgaataccga ttgggacaga tgataaggat attttaaata caatctatca   18960
agtattagag aatgacgggt ataaacattc cttcgatata gtagaaaagg ttttaacagt   19020
aaatatatta taaacagtaa ttttaaagtt atgaataaca ttattaagt tggcgaaact    19080
ataaacgcaa aagagtatat gacatcaaaa gagattgcga caattacagg aaaaccgcat   19140
aatgatgtat taaagctat acgggcaatg gagaatgctt gggtgaaagt taacggggga   19200
aatttttccc tcgttgaata cacggacgcg aaaggtgaga agcgtcctat gtataagctg   19260
acaaaaacag agtgcctgta tatgcaaaca aagttcaaca atgaagcgag gcgcaaaactc   19320
gttatccggt gggaggaact cgaaacaaag gaaagacaaa atgtacctgc tcttcctcag   19380
acatatttag aggccttgaa agcattagtt ttatcagagg aacaaaagca agttcttgca   19440
ttggaaaatg aatcaatgaa gccaaaagcc gattatttcg atactttagt agaaagagga   19500
agtaattaa atctaagaga tacggctaag atgataggag tttctgaacg tttctttata    19560
gaatatttgt tattgaatgg atacttatat agagatgcta aaagaaaatt aaaaccgata   19620
gccaaatatg taggtaagta ttttgttcta aaggaatggg tcagaggcga aaatacaggg   19680
tcccagacat tagtgaccgt gaaaggaaaa gatagattct ataaattaat caatgagtaa   19740
tcaattttaa aaattaatca attatgaaaa cttcaaatta tttgttcagt gttttagtag   19800
gtttgtgttt gatggcaatt gccgcttccc tttcgtcttg tggcgatgaa gaaatgaagt   19860
atgaaactaa ttattcggtt accgttccgg agtggcaaac ggtgtacgta gagggtgagt   19920
gtacaacgaa tgtagcctta tatgtttggg ataaggtaga gttaacgtcg gactacgtta   19980
aggtatattc aatgggacat gtgaattatc tgaaagttac ctatactgaa atggatattt   20040
acggctttat catttaccac attgatagct ataacaaaga aactattcaa taccacccga   20100
aagacggtgt tcttcgacac tctcagcaat taaacgagc tgaagtaacc gttgttttta    20160
gaccattaca ctaacattaa aaccttccgg cgtacaggtc aaccgggtaa acaacagatg   20220
aaagatagaa taacagaaaa ccaattgcag ctaattacta aggataaaga gctgtcggag   20280
atgatagagg gaatcactca gatacgttct attgtcaaag aaaagatgaa ggtatatgaa   20340
tgtataacat atactgagga cgatataaaa gaggcaaaag cagatagggc aatgattaac   20400
aaatcgtcta aagccttaaa cgatacccga atcgaactcg aaaagatata catgcagccc   20460
tttaacaagt tcaaagatgt agtaaaggat acatgcgaca tgttagacct cacctcaaac   20520
aacatagatt cacagataaa gaagttcgaa caggaagcaa aggacgcaaa gatgaggaca   20580
ataaggaagt attttgacga acacaacgag taccttataa attttgaccg ttgctttaaa   20640
tcaaactggc taaacaagaa taaaggtatt gctattgtcc gggccgagat taacgaactg   20700
tttgaactgg tagcggctga cttcgagaaa ctgaaagagc attttgaggg tgaaccttgc   20760
tacatggcta taattgaccg ctatcaagct acgttggact ataacaatac ctaccaatac   20820
ggtgtatcac tcgttaataa ggcactggaa gccaccacag cgctaaactc gcctcagacg   20880
actaatacac aaccaccgca acaacaaccg ctaaaacagc cggaaaacaa gcctcagaac   20940
gaacaggttt atgtaagagc gtttaaggtc aaagtaacaa gggaacaagc atttgcactg   21000
gctgacttta tgttctcaaa caacattgag ttcgagagca ttaaactata gaggggata   21060
tttccctctt atttttattcc attcacaaat gttaattcca tgttaaaact taagtttttt  21120
ctttgtgtta taaatttaat ttttatattt gcagtgtcaa aaggaaacaa agtactaaca   21180
atttaaaaac aaatatcatg gttataaaaa caaggtttaa tataggcgat aaagttctat   21240
ataagggaa tgaatttacg gttatttcta ttgattgtat gaagaatgaa cgaacttttc     21300
tcatacatta tgtgataaga cgtgcaggat tctacgatag aactattttg gaatggact    21360
taattaaaat gcaagttaca caaaactgaa attagtgata tataattggt aaacatatta   21420
taattaacaa attatgaagc agtatttaga tttactttct tatgttttga attatggcga   21480
```

-continued

```
aaagcgagag gatagaaccg gaacgggaac aatcagcgtt ttcggaagta ctcaaaaggt 21540
ttacgatctt cgtgacggct tcccgcttgt cactacaaaa aaggtattca caaagggtat 21600
tatccatgaa ttattgtggt ttattaaagg tgataccaat accaagtacc taactgagaa 21660
tggcgttcac atttgggacg catgggcgga caaagacggt aatttagggc ggatatacgg 21720
tgcgcaatgg cgtgactggc gtgttaatag tcggacaagt atagatcaac ttaaatcagt 21780
cgttgagatg attaagaaag acccgtcgtc acgtaggtta attgttaatt cgtggaacgt 21840
tggtgacctt gataaaatga acttacctcc ctgtcattgc ttttatcaat tctacgtatc 21900
aaagtacgga tttttagact tgcaattata tcaacgtagt gcagatttgt ttttgggtgt 21960
tccgttcaac attgcgtctt attcgttgct tcttgctatg gtggcgcaag tatgcaattt 22020
gaagcctcgt aaattcattc atacgttggg tgacgctcac atatatttga atcatgttga 22080
acaggtaagg acgcaattag atcgcattcc gttgcgattg ccggaactgg ttttgaattc 22140
ttccgtcaca gatctgttcg attttaaatt tgaggatata gatattattg attataacag 22200
ccatccggca ataagagggg aggtagcagt atgaataaaa atgaattttca taaactctgt 22260
ctttgtgaaa caaggaaaac agtcagagag gttttgaaga ggcaagatgt tttaacactt 22320
caaatgttga aacgtagttt taatacttgg tggttatata gtgatatttg tgacgctatc 22380
aattataagt tatcaggtat gtaatttaaa aggggagtac aacgctatgt attccccttt 22440
ttcgttctat cctcacggac taaacgagtc aataaacaat aagtagtaac aagtatttaa 22500
gaaaagttct acaaaaatag ttctaacagt cgttctgtgc gtatctttc agtgttttaa 22560
atttcattaa caataaaatt aaagaaattc tttgtgtatt taaagttttg ccttatcttt 22620
gcattgttga attaagtaag taacaattaa aagtagtata tatgaatcag aatgaagtac 22680
atgtttgtcc gtattgcgga ggcgatttat acctttggca atcctatccg gtttttagca 22740
aagcatattg cgattacgat tgtgagccgg aacaagaaga agaaaatatc tataaatgca 22800
gtgaatgtgg aagggaggta atagatgtcg agtgattta agattaatga agccattta 22860
aacgctaagt tgaagggctt aaaagtgagt aaaaaagaga tagctgaaat gttgtgggag 22920
gatacaaagc caaaatcaag aacgttaac atgtcctcac tttgcaaccg taggacacga 22980
aagattaata ttgaatggtg gtcaaagata tgtgaggcta ccggagtgga cgcaaatttt 23040
ctgtttaaca taaaaccaaa aagcaatgat taaaaatttta tcaaagattc aaaacgagat 23100
gaacgttaaa aaaggacgtt ataataagtt cggtgggtat tattaccgtt catgtgagga 23160
cattttgcag acagcaaaag aagtgtgcga caaatacggt tgttatgtga atgtaaccga 23220
tacaattgag tatattgaag gtagatttta cgttaaagcg actgcaaagg ttgtggatat 23280
agaaaccgga gaatcagaaa cggcaaccgc atttgctcgt gaagaagaaa gcaagaaggg 23340
aatggacggt gcacagttga ccggagcaac ctcaagctac gcacgaaaat acgccctctg 23400
tggacttttc gcaattgatg atagtataga taacgattca ttaaacgaaa cgcaggaaaa 23460
cgaagaaaaa gcggcaaata agaagggttc taaatcttca tcaacaagtc gtccggataa 23520
ctcacagagt caaaacagcta ttttggtagg atacgtcaac gagtgtacaa cggttgagca 23580
actaagtagc ttgtttaaag ctaatcaagc atatcaatcg gatagtacat ttatgaatgc 23640
gctatctaag aaaagagccg aaattgaaaa aagaagtaa ttaacaataa aaattaataa 23700
gtatgaaaga tattataaca ttccccaaac ttaatcaatc agatgttatc tacattgaag 23760
aaacacatga gtatttcaca ccggacttta aaaaattgca tggtataacc ggatttatca 23820
acgagcaatt gtttcccggt aaacttgatg gtattcccga aagcgtttta gcccttgcca 23880
ctgagcgagg gaaacgagtg catgaagaat gtgaaaatat agataatgaa ggaattgaag 23940
ccgaatcaaa acaaggtgaa aactatctca gattgaaagg tgacttcgga ctaactcaca 24000
tcgcctcaga atatatagta acagataacg agtttattgc atcaccgatt gataaggtgt 24060
atttaggcag atactccgac tccgttatat taggagacat aaagactaca tacaaattag 24120
acatgttgta tttgtcttgg caattgtcaa tctatgccta ttattttgaa agacaaaatc 24180
cccatttaaa agtagatact tgttggcta tatggttgag aggtgaggat acagatggta 24240
ttgtgcaggt tgagcggata ccggacaaag agatagagat atttcttcaa tgctgcaaag 24300
aggaattgaa atacgtagat aattgtagtg ctgattcata cgttactaaa ttaaacgatc 24360
ttcctgcaaa ggttagcaac gttgaggaat cagtatatca gttaatcgaa atgcaaaaga 24420
cgcttgacga gcaaatgaat aagtttaaat ttcagttact cgaaatgatg aaagaggcga 24480
aagcatataa tatcaaaggt gacttgatta caatcacacg aaagaaagca tatagcctag 24540
aatcgcttga tactaaagcg ttgaaagaga agtatccgga tatttacgaa gaatttatta 24600
aatactcaga cgtgaaagaa tccatccaaa ttaaagctaa ataattatgg ttatagatga 24660
aaagatagcg aacgagatcg gcttagaggc tgctgccgtt tattcggaaa tgattcttat 24720
cctctgcaca ggaatgtaca gagaaaagtt caaagggtgc cgagtaaagc aagtgcctaa 24780
cactgttttt gttcgatag caaagctaaa agagatcatt ccgttcatgt ctacgaagaa 24840
gttgtataac gctgtaaatc gcctcgtatc ggctggatac ataagagagg caaattacag 24900
gttacccggc atgaatacga ctaaatgtta tcagatggta gatagataga cccggttctg 24960
attgtgatat gcaccccact tgcaagcgtt gtgagtgggg tgcttttttg taaattactg 25020
atattcacat tggttacaat agtgccgaaa attcagctat attcactaat aaatggggtt 25080
actattttgg aaaccctac tcaaaaacat aaaagggata ttagtttaac taatacccctt 25140
tgggtctgcc tattttcgg catacccatc aaatttgagt tgctctaatt atcagacggt 25200
tgcgaataat taaatgttaa agtcaaaaac aataatgttt tttgtttgca accaaaacta 25260
ttttatcattc tctttgtgga gtcaaatcaa aaaacaatat acaacatgaa tttagaacca 25320
cttttttaaaa ttaaaaatgt cgctgattat atgcgttgta gcccaacttg ggtaatgaag 25380
ttaattaaag cgggtaaatt ggaacatgtc aaaattgacg gtgcgtattt cgttgttctt 25440
acaggtgaag aacttgaaaa ataacaagag tttagaaagg agcttgacga gttgttaagc 25500
aaataataat taataattaa aatttcaaat tatgaaatct aatttgtcta aagttggcga 25560
aactataaac gcaaaagagt atatgacttc aaaagagatt gccgaaatta caggtaaacg 25620
acatgcagac gtaatggaat ctattagagt tatggagatt gcttgggtaa aaataggtcg 25680
acggaaattt ccgttaacct cttatataga tcaatgaat agagaacaac ctatgtataa 25740
gctaaataaa acagaatgtc tgtatatagc aacaagttc aacgatgaag cgagggcaaa 25800
actcgttatc cggtgggaag aactggaaag agctaacagt atgggaact ttaacgttcc 25860
taaatcatcc gttacttgc tgccgaacaa caagaagtta ttgaaaacca 25920
acaaaagcag attgaggaaa agaatgcaaa gattgaggct gataaaccga aagttctatt 25980
cagcgaagcg gttgaagcgt ctaaaaagtc tattcttatc cgtgaacttg caaagataat 26040
cactcaaaac ggttatcaga tcggagaaaa gcaactgtat gaacgcctca gaaaagcggg 26100
ctatctttgc agcgtaggag agtcacgcaa tcagccgtct caagcatata tgaacatggg 26160
tctgtttgag attaagaaac gggtgatagt aactggtgag gaatctaagg tttgtacaac 26220
```

```
tacggtttta actccaaaag gtgtgaaata tttcataaat aaatttatag gaaaatgaag  26280
aatgatctaa caggtatgaa atttggaaga cttaccgcta ttagtgttag cggaaaggat  26340
aaatgggta  atttttatttg gagatgtaaa tgtgattgcg gtaactataa aaacgttcgt  26400
gcatataaac ttaaaaatgg gaacacgaaa agttgcggtt gttatttat  agagtcgctt  26460
tcagaaagat caaagaagca tggtttgtta tccggaggta aaccaagaat ttttaatact  26520
tggaatgata tgaaagcaag atgttttaac aaaaatgaaa tagcatataa gtattatggt  26580
ggcagaggaa taacggtttg tgatgaatgg cttgtttttg aaaatttcta taaatgggct  26640
atgttaaacg gttatagtga tgaattaacc atagatagga tagataataa taaggggtat  26700
tatccggata attgtagatt tgtgactttg catgataatt caataaggca gagaaaatca  26760
ataatgataa aaataggaa  tactgaagaa tctgcaagcg gatgggcgag aataacaggt  26820
ttatcaagaa ctgttatagt caatagatac agaaagtatg gatatgaaaa attcaaaaaa  26880
gctgtcatat cttacattca agaaccaatt ggatacaagc attttgataa tttattaaat  26940
aacatggcag ggtaatacccc gcctataaaa acaaataatt atggcattaa gtaataaaaa  27000
ctatatcaat ataccaggcett ggatggttaa ggagttgaat ctaaccggaa atgatctgat  27060
atgctacgca ttgatatatg gttttagtca agacgggaaa agtgagttca acggctcctt  27120
gtcttatata gctgagtggc taaatacgag cagacagacc gcaagactta ttgttaaacg  27180
tcttgtagat aatggagtta tagagaagcg tgacactgtt ataaatggag ttaagttttg  27240
cagatatgta gccataaaata cggggtgtgt tgaaaatcgc cacactgtaa tgataacaa   27300
tacggggtgt ggtgaaaatc gcccacaggg tgtggtggaa atcgccacta ataatatatt  27360
agataatata aataataaca ctaaatctac taacgtagat tatagtgtag ccaagcgcga  27420
agaaacggat ttattcgaag ttgaatcaaa taacgatcct atacctccg  agatattgg   27480
attcacagct aaaggacttg acgtaacaaa gaaaacaatc gaaaggacgg ataatctatt  27540
tactcagcta acatttcctt tcgagtccga ggactttaaa cgcttattct acgttctaat  27600
gactcaacct aaatgcgtg  taaagacaaa gactctaaca gctatgcaag ctaacttaaa  27660
cgagatagcg caatttgaag aagagtttgc taaaagcctt attcaacaaa gtatatcgaa  27720
agggtgaatg tcacttgtgt atgaatcaac gccaaaacaa tatatgcaat ggctgagaga  27780
gaaaacggga gctactaacc aatatcagca aaacaactct cagcaatata agacaaagca  27840
gtattttgct aatgacgagc accgggagat atacgagata tacctaacag agacgtttga  27900
ttaacgagaa tggcatttac cttgcgaatt taagactttc ataataaaaa cgagtaatat  27960
aacatggaaa tagagaaata tcaaaataga ggcggaaaag tggcttttatt gggtggcgta  28020
cttccgtcat tcgtagagag aaacagagaa ttaatacagt ctaataaaaa aaagcagctt  28080
tctaaggtgg atcaacgtat atttgtagaa tctaccaaac gtttaatttc ggaagaagaa  28140
agcgaagaaa agaaaataga gtatttaggc attatcttta tcggggtatg ttctgatttt  28200
ggtctgaatg caccggaacg tagtgcggtt aaaagcgtat tttcctcgat ttttgacgtt  28260
attgatttgt attttgacga tctttcattc gcagaggtta aacttgcttg gcggttgctt  28320
gctgtcgggg aacttgataa ctacctacct aaagatcgct acgggaatcc ggataaaaac  28380
cactacggta gcttaaatgt cgattacgta acgaaggtat tgaaagcata ccgaaagcgt  28440
aaagctgaca tgatggcaaa aactactgcg ctatttcctg ataagccgaa agcgactccg  28500
gaacaagaaa gagcgttttt aaacgtacag gctaacaact ttattttcgc tattatgaag  28560
tataaatata gcggtcgctt taaggctgaa tctgataggc ttataagcga gtcaacgttc  28620
aagtatatgg aacggtttggg gtatgacatg gatactatac cgacatacga ggataagaag  28680
ttagctttag cgcaatttaa aggaagaccg ataaacagct ttgcacaagt gtttgaaaag  28740
gaatgtttag cgactttcgg aattgaacat gaagccgttt ttttcgggtc tttaatgata  28800
gcaaagaaac gtttgttatt ccggtactgg gacgaaatgc tgatagagga agatagcata  28860
aaagatttgt attactataa acattaaaaa catggaaatt aatatttag  ttggaattga  28920
ccccggtgta tcagccgggg gaatagctat ttataaacct ggaagccgc  ttgtaacggt  28980
taaaatgccg gaggatcctt tggatatata caggctattc aagaagatta agcgttccgg  29040
tagcccgatg attgttgttg agaggctgtc aattaggggg gatgataccg gaggtaagca  29100
atatcgcata gttactatgc ttgaaaatta caacaaccatt gtatgctgtg ctaaagttct  29160
cgaaatacct ttagtgctcg ttactccgat gacgtggcaa actggtttag gcctgagggt  29220
gaagggggcg aaaggata  agtcgctgag aaaagagaag tattttcagt ttgcggcaca  29280
ttcatttccg actggtaacg tttttaagtg gaatagtgat gcggtttgca tacttcgctt  29340
tactcagttg atgatagcta acaagcctag gtggatatcg gagcatttag ccaacaactc  29400
agattacgtg ttttctttg  atttaacgaa cgattccatt gaatatgata gattactcag  29460
agataaaagg aaagttgaat atcggtcaaa taaatagcaa aatagcgat  gttttgattc  29520
aagctgtcat aagaatgcga gggaagcaaa agagatacga agattcggt  gaaaagtaca  29580
gggaagcgaa agaggcggaa gaaaagaaag tagatgatat tatagcaaag ttgaccgact  29640
cacaaggcag cttattctaa acaaaggtta ataacgggt  atttcggaaa gatttacccg  29700
ttattatttg cgtataatta agttttgat  ttaatttgca atatcaaaat taatcatagt  29760
agtaacgatt taaaaactta ttaaagtatg aatactaacg aaatgtcagt tgctgatgta  29820
attaaatcac cggagtttaa agatgaatta acaaatcagc tttgtactat gcgttcagat  29880
gttgaacgag ctaaaaacaa aattctgaga atggaggat  tgacgaagcg gattatgtta  29940
gatcgcattg acgatatgac tgtttcggac attatcgaag aatttgagaa aattctactg  30000
agaagagcg  atctccctgc tgccgttcgt ggttttattt cttctttgtg tggtagtgta  30060
tttgctaagg tattttctaa aatgaaacaa aatgaagcaa aacaggataa caataccggg  30120
aaaagtaacg agtaacggac agttgcagat gtacatgggt gagttaaacg agtttgcgaa  30180
actgcacaag ggaaagaata tcatagcaag ttttagcgtt tacgagcctt cgcaatcggt  30240
tgccatgaaa gcgtattact acaaagttgt agtaccacaa tttcaaaaag gaatgtatga  30300
caatggtaat agatggagcg aaaaagacac cgaattgtac atgcggaact tgtgtccggt  30360
aacaatgggt gaggtcgttg atattgatac gggtgagtat cgaagtgacc cggtaagtat  30420
caacgattta tcgaacagtg agtttgtaga gtatattgat tttttaaaac agtttgcagc  30480
cgaagaactt ggagttttta tagaggatgc aacaaaatac gtaaagaaat gaagaagtt   30540
agggtagaag attgcgaaat gacgttgaga gaaaattcg  acttgatgtg cgaggctctt  30600
tcggtgtcac cggatgctat tttaagccgg gagattacga agatattc  aattagaaga  30660
aactgtatta ttcatcagtt gtatgattat cgtttggacg gtttgccgga gctattggat  30720
aggacgaggg ctttaaatagt gatagcgcac cgcaaatttc aaaaccaatt agaggttaac  30780
gatccgttgg ctattgagta taagcgatta attgatgaaa gattggagag ttatttgaat  30840
ggcgaagaag aataaacaaa acttagtcct cgttcattgt acagaatgta aatatagctc  30900
agaccatcac aatttgatat gctattgcag caaaagaaaa caaaagttat gcagttgccc  30960
```

```
gaatatcgga agggtatgcg aacattataa acctaaaaac gaatattagt atgttgtacg   31020
acaattttga attaaagaga gtaaagttca ttccaaacgg tttgaagta gattacaatg    31080
actgtatgaa tgttgacggt gaaacggtta aaacgtttca taaagtgaag aatccggagt   31140
accctcaccc cgatttgcag aacgaagccg ggaaactgag agggtatatc gtctggctta   31200
tgggtctgat gaattttgca aaaatcacct acttatcga tctttcaaaa ctggataagg    31260
agttggataa gcagtttcaa gacttctttg aaatacagtc gactcgaatt atgattagag   31320
agattgtgag agatgaagaa aagaacacag taattatcaa atacgagttt tcaggtacag   31380
acttgtcgct gtttaaaatg cagactccta aaatcaattt ggagggtgaa atgcttcaat   31440
ttgaaattga catgaatact gacttagagg gtatgaagca cgaaatattt gattatctgt   31500
ttaagggtaa gcgtgcacaa cttttcaatgt tcggtgagat tgcggaggcg gacgatatta   31560
aagacgctga tgacgataca gagggtgatt cctttttga cgaagaaact gaaagcgatg    31620
tatctgctga gtagtccgga agaaatagaa tattgcttaa gtagggata taatcccctg    31680
cttttcaatc gatatttcga tatagaccct aaagcaaggt atcagtattt gaaaagtcta   31740
ttcggtgact gtcacgatca gagggcaaac gagcggtttt ttcggtatat gtgggagatt   31800
aagcctcact attgcgaaga atgcttgaag ccgttggaag ggtactcagc cgtttatatt    31860
tcgcatattt gcactcgagg agcattcccg atgttagcgc atgacccccg aaatattaac    31920
atactttgct ttgaacatca taatcagtgg gagcacgcta acacccgaaa gggaatgcgt   31980
atttatcaag aaaatttaga gaaaataaaa gtcctcaaaa gggacagttt aaaattgcaa   32040
aagaaatgaa attagtaaaa tttaaggtta aaaacggaca acacatttg gttaatgcca     32100
attgtgttac gtctattacc aaaaatacaa acgatactac gaatgttaaa tgtgctggtt   32160
ctgattgtcc ttttatcgtt ttgggtagta ttgatgaagt cgaaaagaca ttagtcaagg   32220
gaagtaaagt agattcaata gccggcataa tggttatttt attcataggt atttatatat   32280
tatcaagtat tctaaattta ttttaatatg aacttaaaca aaattcagtt gattggtagg   32340
gtctgcaatg atcctcaagt aaaaacgttc gataatgggg gtaagatttg caacgtgtct   32400
atcgctacaa acgaacgtgc atataaaacg agtagcggcg ttgaagttcc ggaacgaaca   32460
gattttcaca acgtggtatt caaaggaggt ttagcaggta tatgtgagca gatgttgct    32520
aaaggtatgg agttatacgt agagggtact ttgcattatc ggaagtacac agactcgaat   32580
aacgtagaaa agactattgc ggaaattatc gtttctaaca tgcagatggg agcaaagcct   32640
ggaggcaata gcggtcagcg ggcggaatct gccgggagtg ggggtcagcc gccagtacaa   32700
ccgacaccgc caccatcaca agccttaaaa gaacagcaat ttgcagatga tttgccattc   32760
taaaaaaaag gggatactct aaagcagggt atcccttttt gtgttaaata agtgttaaag   32820
attaaatttg taattagaat attaaagttt tgctttatat ttgcaatgtc aaaaggaaac   32880
aaagtaataa caattaaaaa ttaaccaata tgacaactta catttataaa ggagaaaaga   32940
tcagtcattc aaagttatta atgcttttgc gttctgacca cgtttttggc ggaaacaagc   33000
tatcacatta cgaggcttta gtgaaagcgg ctgagaatgg gaacgagcgt gcaacaaata   33060
tccttagaga tttagaagta aagtaataac aattaaatag tagaattatg gaaaaagaa    33120
gaatgtccgg agagtttaag atttcggtta atagactaaa cgaaagtact gggttatacg   33180
aagacggtgt aagcgttgta actgggttta tgtaccaaat cggtgcttat caatattttc   33240
tacactggga taaaacattt cagagggtag atataacaga gtcaagtaca gggtttagag   33300
tgaaaagtat tgagaaattg aatggtgaga cacctaaaca gtgccatgat agagcaatag   33360
aggaaatgaa gggttttaac ccgtctttgg gtaactggga aaaagctaaa tcaatgatga   33420
agaaagccgg aatacctttac ccgttgaacg aatggataac taacttaaag gacataaatt   33480
caaatgaaga aatcaagaaa gattaatcga cttaaaagtc gttttgttac ggctaaattt   33540
agcttaaagg aacaaagaca gtttaccaat attttgagtg aaaaaagaaa aattagaaag   33600
gatagggata aaaccttcga ttctctttta gaacttgata aaattatatt gaaagctgat   33660
ttatactgtg caggtttggg tgaatttgtg ttttctgaga gtgaaatgga ggcgtttagc   33720
aggtttgaaa aagtaaaaag ggagttttat catggaaagt aaattaaatc agttagaagt   33780
ccttattttg caggaagaag aagcatacaa ggacatgcga gtagcagaga aaagacatgc   33840
cgcatgttta caagaattgt cggaatttga aagcaaagct aaattaggaa acattcgata   33900
ttgcggaaac tgtgtgtatt ttccaagtgc gaaaagagga ggaaagtata agtgttcgtt   33960
gaccggagag aagaaagatt attgcagtga gggatgtgaa aaatatagtg aattaccgtt   34020
ttaaaaatag aaaaatatga ataatttgat taaagttagc gaaactataa acgcaaaaga   34080
aactatgtgt tcaactgaaa ttgcggaatt aacaggtagg agacatgata acatcataag   34140
agacataagg gggttattat cacagggcgt tgccgtcctc aatttgagg aggggacata     34200
taaggatgct aataaccaaa atagaccttg ttacaatctt acaaagaagg gttgtttaat   34260
tctcgcttcc ggatatgatg ctttattgcg tgaaaagata attaacagat gggaagaact   34320
tgaaaaggag aagcgtttcg gcaacttcgt tattccatct acatttagcg aggctttaat   34380
gttagcagcc aaacaagcgg aagaaataga ggagaaaaat aaattgctgt tagagcagac   34440
tccaaaggtt gagtttttata atgctgttac aggtagcgag gacactattg atatgcgaac   34500
ggttgccact gtgttgaata tgggaatagg tcgtaataaa atatttgagg tattaagaga   34560
taaacatgtt cttgatcgta aaaacatgcc ttatcaaaag tatatagatt tgggatattt   34620
tagaaccgtt gaaactcaat atacaaaag tgatgggacc aactgcatta atataaaaac    34680
tgtggtgttt caaagggct tagatttat atgcaaaaca ttaactttaa ataaataaga     34740
tatgattgat tttagcaaaa gcgttatttt tttaacaaaa gaattgaaag aacagcatga   34800
aagaatgaag gaaaaaggtt tccatgatag aaatgtttct ttgccggaaa tattcgggct   34860
tatcatttcg gagatgtgcg aggcgatgga ggcggaaaga aagggaagaa ctgtggaaaa   34920
cggaaagtac acctgggtgt tatcatataa ggaagatgaa agtttcaagt cgaaatttaa   34980
tcaatgcata aaagatactg ttagcgatga acttgcagat gtattatcc ggtagttgga    35040
cgctaccggt aaatataacg aggataaa cgatatgac actttaaac actgattga      35100
tgaacgtgtg aaaattctaa aaaaaactcc gaatacattc gcttattacg tatataatct   35160
cgcatactgg gtaacaagta atgaaaaaat atgctgcaat tactttacta ctataatgga   35220
gatatgtgca gcaatagcaa tcatacataa cattgattta ggtagagcga ttgaggcaaa   35280
aatacggtat aatgaaacaa gaggctacaa gcatgggaag aaatactaat aacaaaatag   35340
ataaaaatat gaatttagaa caaatcaaga ttaacgctat tttagcggct gatccggagg   35400
gtattcaaat agacggtaat cactatcaag gtgattctat tcctttgtat cagtttctca   35460
atcagaataa tgttaataca atggatgct atgtgataaa atatgcattc cggcatagac    35520
gtaaaaacaa agaagagat attgcgaaag ctattccatac tctacaattg atttttgaaag  35580
acgaatacaa catgtatatg ttaggcggac agttgtacac gaaagagcaa tatgatgaat   35640
tgctcagcca ggcgaaaaga gaggcggaag gaaaagaaac tgaaactacg gtgatatata   35700
```

```
ccgataaggg gatagatatt aactctgatt ctaataggaa tattaatagg aatatttacg  35760
ttcgtaaact aagcgaagtt caagccgttt gtatagatag aactaacatt tcacttgacg  35820
atttgcggga catgggcctt gtgcttaatg cttacgaaat gggaaagggg gcatatgtta  35880
ccagccaaaa cggaaaggag ttttatgtta aatatggatc ctacatttgc ctctcagagg  35940
atgggtatta tcaagtttat agcaagagtg aatttaaaaa actgtttgag cctaaacaat  36000
aataaataaa atgtaaatta attcaatacg tgattaaaaa tgaatgaatc ggtagatata  36060
tttggaaata aggtcgcttt cataaaacca tcattaagca aagaaaaaga aaagacgctt  36120
tttgatgact acaaaaactt tgtgaataaa tttaaaacaa agaaaactac agatgattgc  36180
tacactccgc ctgaggttta taattgcatt ttgagataeg tttcagaaaa atgtaatata  36240
agaggagcgg aaatagtacg tccattctat ccgggtggag attatgaaaa ttgtgaatac  36300
ccggatggat gtatcgttgt cgataatcct cctttctcta ttatttcaca gatagtaaag  36360
ttttatatag aaaaaaatat taaattcttt ctgttcgctc cacacctgac gctattctcc  36420
caaagggtcg aatgttgccg aatagtagtt ggagcatcaa tcacctatga aaatggagcg  36480
aatgtaaaaa catcgttcat atccaatta ttcgatgatg ttacggtaat gtctgatca  36540
tttctttaca gagagctcga aagaataaac gaatcgaaaa aagtgatgct tccaaggtat  36600
aagtatccaa acagcgttct aaccgtctca gacatgcaat ggtgcgtaga acgtggtgtt  36660
tcaatgcgat ttaagaaaga tgatatctac cacattaggg gacttgatag ccaaaagcca  36720
cataagaaag gtatattcgg tgcaggattc cttctttcag agagggcggc ggcagagagg  36780
gcggcggcag agagggcggc ggcagagaag gcggcggcag agaaggataa tattataatt  36840
tgggaactgt ccgaaagaga gaaggaaatt ataaaatcac tgggtgaata aacctcaata  36900
tactcaaaaa gtttaaacct gaatgaaacc acgttgtaag tgttacagcg tggttttctt  36960
tttgcattca atttaataca cctatatttg catagacaat caattcattt ttagcaaagt  37020
gaatctattt ttgtttaaat ataattctta atgatatggt taaagtaggt agtatgatta  37080
aatcacaagg aaaaataaag agaacggacg aacaatggga ggctgataaa gcacttgaat  37140
ctgaattgtt tctaaagggt tattcttatc gcagaatcag agataagatc aatgagcgct  37200
acaaagaaat gggaatagat atacaaatat cttatcagtc tgtgtataac gacattcaga  37260
aatgttttgc tgagtggaaa cggaacaat tcactaacat agaccagtat gttacacagg  37320
aaattcaagc actcgacaat gtggcgaggg aggcgtggga ggaatgggaa cgttctaagc  37380
gtcctaaatg caaaacgaaa tacaggttta aaactgctgt cgaggtgcaa aaggaaacta  37440
ctacgggtga cccttcgttc ttgaatgtca ttcttaacgt acagcaaagg aaggcacgtt  37500
tgttgggata tgatagtccg ttagttgttt ctattgtcgg ggataaagaa aaagagaaac  37560
caaaatacga cttatccagt gttccggagg atgttctcga aaaaatggcg gacgctttgc  37620
agaatggagg tgacgatgaa gataaataat ataccaccag aggaaattgt taagcatgtt  37680
gcgagaaaca agttcaagaa cttcgctaaa tacgtagata atgaaattat attaagccag  37740
tttcataaaa cgtattacga aattcttgat atgtttgcgc atggaaaaat aaagaggtta  37800
atagtttcga taggaccgca gcacggcaag agtgaaggta gtagccgcaa actacctgcc  37860
tttatacttg gtttacgtcc ggacgccaag atagcaatag gttcttatgc tgcaacgctt  37920
gctgagggct tcaataagga catacagcgc attttagata caccggagta cattagcttg  37980
ttcccaggta ctcgtattat gggagcgag aaacatcac gttacgaagc gtacaccgt  38040
aatagtaaaa tgactgaggt tgtaggtcga aaaggatcgg ttacggctgt cggtcgttcg  38100
ggtggttttaa ctggtaggtc cgttaacgtt gctatcctcg atgatgttta taggatcac  38160
ctcgaagcca actcacctat tattagagaa gccgcttgga agtggtacac tacggttatc  38220
agaaagcgtc ttgacaataa cggtcaggaa cttatcgtat ttacaagatg gcataaagac  38280
gatttgatag gtcggattga gaagaaagag aaagttatta cggtgacgaa atggtctgat  38340
cttgataata taccggaggg cgcatggta aagataaact ttcctgcatt gaaggttggt  38400
gagccgacag aaatagaccc acggcatgaa ggtgaggcgt tgtgggaaga gaaacatagc  38460
gcaaagaaac ttcttgctga gcgtgaactt gacaaggtgg aatttgagtg cttgaatcaa  38520
gggaatccgg gaagcgcaga gggacagcta tacggaaagt ttaaaacgtg gtctgataag  38580
tcagatttcg gtgtatttct cggtcgtggt aactataccg attgtgcaga tacaggaacg  38640
gataaccttt gcagtatatg ctatgataaa taccgttcaa aacagccagt ttggagcgaa  38700
aaggaaagaa catacaagta tttaatattc tgccttgtca cggatataat atataccact  38760
gacccgatag aggttacaca ggtgacagtg ccggagatgt taaacagaaa cgaaactgag  38820
tatgctaaca ttgaaagtaa taacggagga cgttcatttg ctgttaatat atcgcctaaa  38880
actaaaacct cgatacgatg gttctctcag cacaataaca aagaggcgag aattttaaca  38940
cacgctgcga atgttactca atctatcgtc atgccgttcg gatgggagtc taaatttcca  39000
cgtttctacg aggacgttac aggctatctg agggactttaa aagcgaacgt acatgatgat  39060
gcaccggata cattgactgg aattgtagag aagaagtta tgcccgctat cgagcctaaa  39120
cggagaggta ttaagcgtat aaactaatag aaagcaaatt gtatctatgt ttcaaaagaa  39180
ataggtaca tttgcattgt taattaattg tttaactaaa aattaagaaa atatgttgta  39240
ttgtaattgt ccgcttggag aggctttgcc ggatatccccg gttgtaacat gtccggagaa  39300
cttcggtcag attcagaaag tagtatttca gagattgatg ggtaaaacgg ctgaaaattc  39360
aataaccgtt gcaactgcta aaacattggg tacttggacg gctttactcg ctgctaaaga  39420
cgctactaaa atggtggttt caccgtacat tgctgagccg actgttgaag cgggcgaggc  39480
tttgacgtat ggaggaggaa acgcaacacc cggtggcgta gttgagattt tggggtctaa  39540
tagtactccg tttactggta aattcttgaa aactccacag acagttatca aggttttgaa  39600
gcaatttatg tgcgaagtta ccggaggact gggagtatat ttgattaacg gcaacggtca  39660
gatcgctgct attaaagaag gtgaaaacta aagccaatc cccgttgaat cgctgtttgt  39720
aggtgatcgc actatcggag gtttggaagc accggacgcg aatgtaatct cgtggagttt  39780
caaacctaac tggtcggata acttggagat tttcaaaccg gatttttaacc ctctgacaca  39840
gttaataccg gcttcgccag cagcctaatg aatgctaaga aaacaatggt ttccctcact  39900
tgtaaagagt tgggggaaac tcgtttattt gaagttgaac atgctgaacg tctttttgtca  39960
atgtttccca aggagggtg ggagataacg gaaggtaaa gctattatt aaaacaggat  40020
gggaaaatca gtcgaagaaa tacggagat attcaaaaaa ccgatcaatc ggaggtggat  40080
acagaaagcg agggacgag aggaacggat agccttttcac gcaaggggtaa aggttgacga  40140
tgtacgtaca aagcctgctt tagacttct taaccgggtg aagatttgga tagcaccgga  40200
caaatacgag atatttaact ctatgttcca tttcccggta aagacaaacg aggttacgaa  40260
cgagatattt gataaattga gtcgtgtgtt tgacggtcgg aatcctgctt ttaactatca  40320
gttcacggac tcggaagatc gggatgactg ggagtattac agacaagaag tactgaaaga  40380
accgcatgtt tgggctactg atggttggga taattcaaa gatagaatta actccgttct  40440
```

```
tgtaattgat ttgccggagg tgcagcaggg tgataaacca gagccttatt tctatttcgt  40500
tgatatatcc tcagtggtaa gttatgaaac tactaaggag gataataatc ttatgtcgtg  40560
gataatgttc aagacgaatg atgaaaagtt gattcaaata gatgatactt tttacagacg  40620
tttaaaatc gaaagaaca attcactcac attggaggtt gaaagtacgc acgatttagg  40680
ttattgccct tcgcgtttct tttggtctga ctctatatca ttgcaagaac cggatataaa  40740
gaaaagcccg cttaccaaag tacttgattc gcttgactgg tatctgtatc aatcaacggc  40800
aaagaaacat cttgatttgt acggtgcttc tccgatctat tccggatatg aacaagattg  40860
cgattatatt gcaacggag gcaaagagag gtgtaacgga cacggtttct taatcggtga  40920
taagggtgaa tatattgcag acatggacgg tcaacctatg aaatgtccag tatgttcctc  40980
gaagcggttg agcggtgcag gttcttatgt agagatacca gtaccaagcg agcagcaacc  41040
ggacttgtca gaccctatca aaatgctaac agctgatgta tctgctttgc agtataacgt  41100
gtctgaggag gaacgtttaa agaagaacat tattacctct gtgactggcg taggggtga  41160
ggttcagaaa gaaacagctg taaacgagaa acaagtacag gcttcatttg agagtcaaac  41220
gacgattcta aaccggatca aacgaggctt tgaggaagca caatgctttg tagacgcaac  41280
agtttgccga ctgagatacg gaaatacttt cgtttcatgt tcgataaact acggcactga  41340
gttctatatc tatacaccgg aacaacttgc agagagatac aaagtactca aagagtcggg  41400
agcaagcgaa agcgagttag acgctatgcg tacacagata atcgaaacag agtacaggca  41460
tgacccaata caaatgcaaa ggttattaat cttgaaagag attgaacctt attctcactt  41520
aacgagggaa gaagcaatta atttgtataa agaaaacgtt ataagtgagg aagatttgcg  41580
gataaaacta aacttgccta catttgtgcg tagatttgaa agagagaaca tgaatattat  41640
agagtttggc tctaatattg attactctaa taagataaac aaaattttag aaacattaaa  41700
acgttatgca aatgaacaga ccattgtacc cggagcaccc cttgacaag gtgacagcag  41760
aaaactatct gtgtccggat aatgaaaaag gtcactatca cgtgattcaa gaaaggttgc  41820
agtttgaccc tgacactggt gcgagagtgt tttcgccagt attgcagaaa tacagacctt  41880
taactttga aatgacggtt tacccgtatt tgagtagagg aggctacaat attagaattg  41940
tgcacgatcc tagaaagtat gcaaaggata tgcaggaata ttcagaacag gttaaaaaag  42000
caaagcaaga acaggcttta aaggaactga gagaacagat cagagaggaa gagagaaaga  42060
aggttcttgc tgagttgaaa aaggaagaaa agaaaggagg taagtaatgt taacggtaga  42120
tattctaaga caaaataaag ctctttcaga gctaacagat gagcagttga atgctattgc  42180
taccctttcg cagaatgacg aaatgcaggt tattcagacg aaagttaagg aggaaagagc  42240
aaaagcgact ttatctctga gtcaagcatt cggcattgac gatgttacag accttacatt  42300
tgaaaaagct gtcgagtttg gaaagaacaa actttcgtct gttgattctg ctaagtttga  42360
aaagactatt gcagatctta aaacagaact tgaagccgaa aaagcaaaga aggtaggtga  42420
taaggataac gagaaaatag ccgctttgca ggctgagtta aacgatacta agacgaagta  42480
ttcggaacta acaaatcagc ttacagagaa agaaaaagag ttttcaaaca agctatccga  42540
ttataagatc acttccata ttacacaggc tttaggcagc atgaagtttg aaagggagt  42600
taatgacgct atgttgaata ttatcaaaca gcaagcagtg aacgatctta aaactcagtt  42660
tacgcctacc attgtcgaga aagacggtaa ggaaagtatc gtgtttatga aagacggtgt  42720
accttacaac aatccggcaa acggtctaaa tccttattct gtatctgagt tgctgactga  42780
gaaactgaaa ccgttcggtg tcctcgatga aggaagaacc gtgggaggtg caggaggcaa  42840
aggaggcgga aaaggaacgc caaccgcaat tgatctgaca ggctgtaaaa ctaaggtaga  42900
ggcgcaggag gttgcgcata aatacccttgc cggaaaaggg ctaacagtgg ggtcggaaga  42960
gtaccaaacg gaactcaata caatttggca agagaatgat attcagaacc tgccgttaca  43020
gtaaaaacaa aggggatacc catatttata aactttaaaa acagattatt atgagcttaa  43080
ttgctacacg tacacaggaa atgcggttga gaaatccgca ggtagacaag aacatgagcc  43140
gcctaacaga gtggggtgcg cttgactttt tcctttctca gacgaatgca cctgactcta  43200
tgcttaacga tgaaactaaa cgtagggcgt ttagttctat ggggaccgac atcaaaattc  43260
cggtgattga ttatgacggt accgtcacga ttgcaaacga acgcacatgt gtcattgcgg  43320
acgctgagaa taccctaaa ctgatgacgg ttgtgtggaa aacatacgct ttcgttttta  43380
cgatggtccc gacgatgttt aacaacaacg aaatcgacta tcagaaagat tttgaaaaga  43440
aaatgcttaa attttctcgt aaattcttgg atcaagttga caaggacgct atcgcagcag  43500
tggaaacagc taaaacgcag aagttcggca acctgcttta ctacactcag tcagcaaacg  43560
atgtgcaggt gaattacatg cagcgtaatg acatactcgg agatttgcac ccgatgttcc  43620
gttctatgga ctattccggt caacttcata tcgtaggtga tacaggtgta gacgctattg  43680
ttcggaagtt ggaacaacac ggaatctaca acgatgttaa caagcaactg gaatatgcaa  43740
ataagatttt ccactttaca aataacatgg tttttggaaag tgaaaacttt gctcagttct  43800
acgcaattga aagcggtaat gttggtatgt tgacccgtgt tgaccgcgaa gccctcagac  43860
gagcaacctc taaaacaggt cacgaatggg acgttatcaa cttcccgttt gcaggtttcc  43920
aagttggtac acattactac gagtcggtag gtgatcagtc agaaatcgca ggtcggcaa  43980
ctgctgacat gaaatgtaac atcaaagagc actacggttt ctccgttgat attgctttcg  44040
ttgtagctta caactctgca ccggcaactg tttccaaccc ggttatgaag gttgaaatta  44100
agaaggacgg ttctcagttt ggcggtacac ctgtttacat cacgaatgcc gaacagatcg  44160
gaggcgggtc tgctgccagt gaaatgtctg ttaatattgc taaaattgga ggaaatccag  44220
ttgcagaatc agcttttaag tagatttggg acaaggttaa ggtgcgtca gtttcattca  44280
ctggtggtgt agttgatgta aaggttaact ctcaggcttc aaatcttaat gtagaggtta  44340
aaaacgcaga tagcgcacca gttccaacga aagcagttgg gggatagtag ttatatagta  44400
aattaaagtt taattaaaag ggaggggaaa gaaatatccc ttcccttttt taatttgaag  44460
caacatgtat agaataaaag acataaaaga tagcttaaaa aacgtagtag gttggaggca  44520
gtcatacgat ttaggcagtc agatagacac cgaactaacc acatctgaaa gtggtatttc  44580
ttatcaagac gttcacccac ttgtgacgct tgaaaacata tcatctataa tgccgttaga  44640
ctactataag aagtacccgg aatacagcga tataaagact tatgtggtcg gtgacaaggt  44700
gaggtttaat agtgaccctc tattgtctaa accatctgta tggatagcca caaacgaaac  44760
aaccggagag cagccctcag agggtagtca aaattggaag agatataacc cttttatctga  44820
ttcaga gagttaaacg aaaaagcaat aacggctact atcactaaat ttatcacggg  44880
aaagacgata gcgggggaaa caaagatgct gttagagcgt aggccgctgt ttgatggttc  44940
gggatactat acaaatcaga ttgacccctac aaagagcatg gtaggctatg aattttgcc  45000
agtccgtgcg atgggtgtga ctacaaagat agaaaggata ggtttgcagt ttacgaagcc  45060
agtgaaagtt aagatgtatc ttttttcacag ctcacagcct cagcccatac acacgtttga  45120
cttgaattat actgcaaggg gtgcgtatca atggtttgat gtacctgaca cattttttacc  45180
```

```
ttatatttct gaggcaacgt caccgggtgg cacatggtat ctgtgctacg atcaagaaca    45240
attgccgtat gatgtatttg caatcaacat ggcaaaagac tttagcgcgg agccgtgcgg    45300
aacttgcaac gttggcagcg tacaggcgtg gagagagcta acaaagtaca ttcaaatatc    45360
accgttcagg aatgactcaa aacagggtga gaatctgttt aacattcaat caagcgtcta    45420
tacacctgca acatgctacg gtattaacgt tcagtttacg gtagcttgtg acatcaccga    45480
cttcattgta agcgaaagac ttgtgtttgc gaacgctatt tctttgcaga tggctgctta    45540
tatccttcgt gaacttgcct tgaatccgaa cgtccgacag aatgctaatc agttgaacat    45600
tgatagaaga tcaatcttat acgaggttga cggtgtgtcg caaggacgtg cgcagggtat    45660
cgggcaccag ttaaatcaag caatgaaagc gttaagcgta gatactaaag gtatggatag    45720
aatatgcttg acttgccgga atggtggtat cagatttaaa tcgacatgat aacaaactta    45780
ttagatagag ttaagaaagt gaaagaggct ttagactcag gacgaatagc aaaggaaatt    45840
gtgaggaaca acgataacat tcttatcgac atgaacgcac aagaccagct attcgccaaa    45900
ggggtaaaca ggttgggggt cagaatagac gagtatagac cttatagccc cttcactatc    45960
aaggttaaga tagagaagcg gcaaccgtat gaccgggtga ctttaaagga cacaggggag    46020
ttttacgact cttttttacgt tgaaacggct gaggatagat tttacattaa agcctcagac    46080
gaaaaaacgg actggttgat taaaaaatac ggtgctgaga tatttggttt aactaatgaa    46140
tcgcttgccg aatttatcag cgattatgtg aaagatgaag cagcaaaaaa agtaaaggag    46200
ataataaatg aaagatagag ctattttaaa gccgaatgcg gtacttttttg atgaagtgat    46260
aggaaatgta caggttagcc ttgtaaagtc gctacaatgg ctaaattatg cgtttggaag    46320
cgcatataag ttagtggagc gaacggagaa aggaaagttt gtcactcctt ctgttttatta   46380
caaggataaa gactatttga ggttagaacc aaatgacaag tacggcaaca cctgtttttt    46440
ctatatccac gactcgcaag attacgagga taacggagcg ttcggcttcg gtgatctgaa    46500
aggtga                                                              46506
```

COMPOSITIONS AND METHODS FOR INHIBITING THE PROLIFERATION OF ENTEROTOXIGENIC *BACTEROIDES FRAGILIS*

This application is a Continuation Application of U.S. Ser. No. 17/227,287, filed on Apr. 10, 2021, which is incorporated by reference for all purposes as if fully set forth herein. A Sequence Listing XML file named "20001_0061C1.xml" created on Oct. 31, 2023, and having a size of 48,815 bytes, is filed concurrently with the specification. The sequence listing contained in the XML file is part of the specification and is herein incorporated by reference in its entirety.

BACKGROUND OF THE INVENTION

Field of the Invention

The present invention relates to compositions and methods for inhibiting the proliferation of enterotoxigenic *Bacteroides fragilis*, more specifically, a composition containing a Siphoviridae bacteriophage and a method of using the same.

Discussion of the Related Art

*Bacteroides* species comprise nearly half of the fecal flora community and are host symbionts critical to host nutrition and mucosal and systemic immunity. Among *Bacteroides* species, *Bacteroides fragilis* (*B. fragilis*) strains are opportunistic pathogens. Enterotoxigenic *B. fragilis* (ETBF) can produce a proteolytic enterotoxin, named as *B. fragilis* enterotoxin (BFT), or fragilysin, that causes secretory diarrhea and colonic epithelial damage. ETBF emerged over the past 35 years as a global etiology of diarrheal disease in animals and humans that is accompanied by colitis (Clin. Microbiol. Rev. 22: 349-369, 2009). An association of ETBF with chronic intestinal disease has been established for more than 20 years and ETBF is also positively associated with ulcerative colitis and colonic neoplasia (Gut Pathog. 9: 53-59, 2017; BMC Canc. 19: 879-882, 2019).

In addition, ETBF may cause cancer such as colorectal cancer (CRC). CRC is one of the most common cancers, accounting for approximately 10% of all cancer cases and approximately 8% of all cancer deaths. BFT is known to bind to colonic epithelial cells (CECs) and to stimulate cleavage of the tumor suppressor protein, E-cadherin. E-cadherin cleavage increases intestinal barrier permeability and augments cell signaling via the β-catenin/Wnt pathway which is constitutively activated in essentially all CRC. As a result, BFT stimulates proliferation and migration of human colon cancer cells in vitro (Gastroenterology 124: 392-400, 2003). The ability of BFT to further activate the nuclear factor-kappaB (NF-κB) pathway inducing pro-inflammatory cytokine secretion by CECs and data indicating that specific pools of NF-κB foster the initiation and promotion of epithelial tumorigenesis led to the hypothesis that ETBF were pro-inflammatory, oncogenic colonic bacteria. This hypothesis was supported by a recent small study in Turkey suggesting that ETBF colonization is more frequent in CRC patients than in controls without CRC (Clin. Microbiol. Infect. 12: 782-786, 2006).

Generally, antibiotics are used for the treatment of infectious diseases of ETBF. Here, the effectiveness of antibiotics has been continuously decreasing due to the increase of antibiotic-resistant ETBF, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called "phages." Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. It has been shown that the attack of bacteriophage is specific, meaning that one species of bacteriophage targets only a single species of bacteria (or even a specific strain of one species). In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to ETBF, many kinds of bacteriophages that exhibit antibacterial action against ETBF must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by ETBF includes: a Siphoviridae bacteriophage having an ability to lyse the ETBF cells, and a pharmaceutically acceptable carrier.

In another embodiment, the Siphoviridae bacteriophage has a genome including a sequence as set forth in SEQ ID NO: 1; or a genome that has (1) a sequence having at least 90% query cover with at least 90% identity to SEQ ID NO: 1, (2) a circular genome topology, and (3) 64 open reading frames.

In another embodiment, the Siphoviridae bacteriophage has a concentration of $1 \times 10^1$ pfu/ml to $1 \times 10^{30}$ pfu/ml or $1 \times 10^1$ pfu/g to $1 \times 10^{30}$ pfu/g.

In another embodiment, the Siphoviridae bacteriophage has a concentration of $1 \times 10^4$ pfu/ml to $1 \times 10^{15}$ pfu/ml or $1 \times 10^4$ pfu/g to $1 \times 10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the infection or disease caused by ETBF is acute and chronic intestinal disease, bacteremia, diarrhea, colitis, colonic neoplasia, or cancer. The cancer is colorectal cancer or colon cancer, but is not limited thereto.

In another embodiment, the composition is a solution, suspension, emulsion in oil, water-soluble medium, extract, powder, granule, tablet, or capsule.

In another embodiment, the composition further includes a second bacteriophage having an ability to lyse ETBF bacterial species and the second bacteriophage has a genome that has a sequence having less than 90% query cover with at least 90% identity to SEQ ID NO: 1.

In another embodiment, the Siphoviridae bacteriophage has major structural proteins in the sizes of approximately 42 kDa, 48 kDa, 63 kDa, 65 kDa, 75 kDa, 88 kDa, and 118 kDa.

In another embodiment, the Siphoviridae bacteriophage has a latent period of 10-100 minutes and a burst size of 150-540 PFU/infected cell.

In another embodiment, the latent period is 40-80 minutes and the burst size of 200-450 PFU/infected cell.

In one embodiment, a method for preventing or treating an infection or disease caused by ETBF includes administering to a subject a Siphoviridae bacteriophage; and lysing the ETBF by the Siphoviridae bacteriophage.

In another embodiment, the Siphoviridae bacteriophage includes a sequence as set forth in SEQ ID NO: 1.

In another embodiment, the Siphoviridae bacteriophage has a concentration of $1 \times 10^1$ pfu/ml to $1 \times 10^3$ pfu/ml or $1 \times 10^1$ pfu/g to $1 \times 10^3$ pfu/g.

In another embodiment, the Siphoviridae bacteriophage has a concentration of $1 \times 10^4$ pfu/ml to $1 \times 10^{15}$ pfu/ml or $1 \times 10^4$ pfu/g to $1 \times 10^{15}$ pfu/g.

It is to be understood that both the foregoing general description and the following detailed description are exemplary and explanatory and are intended to provide further explanation of the invention as claimed.

Advantageous Effects of Invention

The compositions and methods for inhibiting the proliferation of ETBF, of the present application have high specificity against ETBF, compared with conventional compositions and methods based on antibiotics. The compositions can be used for preventing or treating ETBF infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
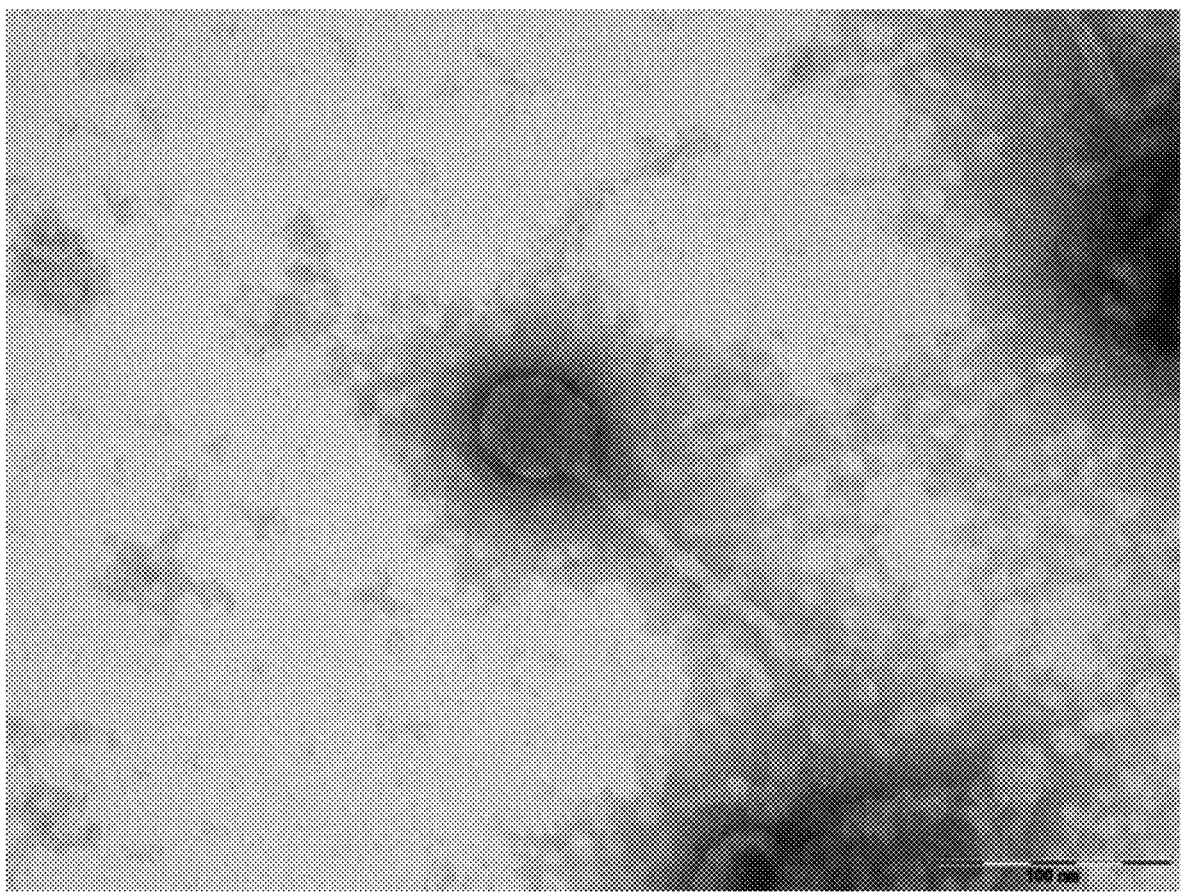
FIG. 1 is an electron micrograph showing the morphology of the bacteriophage Bac-FRP-5.

Reference will now be made in detail to embodiments of the present invention, example of which is illustrated in the accompanying drawings.

In accordance with one aspect of the present invention, the present invention provides a Siphoviridae bacteriophage, named as Bac-FRP-5, which has the ability to specifically kill ETBF and has a genome including a sequence as set forth in SEQ ID NO: 1. In some embodiment, the Siphoviridae bacteriophage contains a genome that has all the following characteristics: 1) including a sequence having at least 90% query cover with at least 90% identity to SEQ ID NO: 1, 2) having a circular genome topology, and 3) having 64 open reading frames; a genome that has all the following characteristics: 1) including a sequence having at least 92% query cover with at least 90% identity to SEQ ID NO: 1, 2) having the circular genome topology, and 3) having 64 open reading frames; a genome that has all the following characteristics: 1) including a sequence having at least 94% query cover with at least 90% identity to SEQ ID NO: 1, 2) having the circular genome topology, and 3) having 64 open reading frames; or a genome that has all the following characteristics: 1) including a sequence having at least 96% query cover with at least 90% identity to SEQ ID NO: 1, 2) having the circular genome topology, and 3) having 64 open reading frames.

The present invention also provides a method for preventing and treating infections or diseases caused by ETBF using a composition including the same as an active ingredient.

The bacteriophage Bac-FRP-5 was isolated by the present inventors and then deposited at Korea Collection for Type Cultures, Korea Research Institute of Bioscience and Biotechnology on Dec. 9, 2020 (Accession number: KCTC 14403BP).

The molecular weight of major structural proteins of the bacteriophage Bac-FRP-5 is approximately 42 kDa, 48 kDa, 63 kDa, 65 kDa, 75 kDa, 88 kDa, and 118 kDa.

The latent period and burst size of the bacteriophage Bac-FRP-5 are 10-100 minutes and 150-540 PFU/infected cell, respectively, preferably 40-80 minutes and 200-450 PFU/infected cell, respectively, but are not limited thereto.

Also, the present invention provides a composition applicable for the prevention or treatment of infections or diseases caused by ETBF, which include the bacteriophage Bac-FRP-5 as an active ingredient.

Because the bacteriophage Bac-FRP-5 included in the composition of the present invention kills ETBF effectively, it is considered effective in the prevention of ETBF infections or treatment of diseases caused by ETBF. Therefore, the composition of the present invention is capable of being utilized for the prevention and treatment of diseases caused by ETBF.

The diseases caused by ETBF in the present invention include acute and chronic intestinal disease, bacteremia, diarrhea, colitis, colonic neoplasia, or cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Bac-FRP-5 is included as an active ingredient. The bacteriophage Bac-FRP-5 is included at a concentration of $1\times10^1$ pfu/ml to $1\times10^3$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-ETBF bacterial species may be further included in the composition of the present invention. In addition, other kinds of bacteriophages that have antibacterial activity against ETBF may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block ETBF infections; and (ii) to inhibit the progression of diseases caused by ETBF infections.

In this description, the terms "treatment" and "treat" indicate all actions that (i) suppress diseases caused by ETBF; and (ii) alleviate the pathological condition of the diseases caused by ETBF.

In this description, the terms "diseases caused by ETBF" and "ETBF infections" indicate acute and chronic intestinal disease, bacteremia, diarrhea, colitis, colonic neoplasia, or cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate," "isolating," and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

In this description, the terms "query cover" and "identity" are related to BLAST (Basic Local Alignment Search Tool) which is an online search tool provided by NCBI (National Center for Biotechnology Information).

In this description, the query cover is a number that describes how much of the query sequence (i.e., the sequence of genome of bacteriophage Bac-FRP-5) is covered by the target sequence (i.e., the sequence of genome of the previously reported bacteriophage). If the target sequence in the database spans the whole query sequence, then the query cover is 100%. This tells us how long the sequences are, relative to each other.

In this description, the term "identity" or "sequence identity" was measured for "query cover," and is a number that describes how similar the query sequence (i.e., the sequence of genome of bacteriophage Bac-FRP-5) is to the target sequence (i.e., the sequence of genome of the previously reported bacteriophage). More specifically, the terms "identity" or "sequence identity" refers to the percentage of identical nucleotides in the spanned sequence part of the target sequence (i.e., the sequence of genome of the previously reported bacteriophage) or the query sequence (i.e., the sequence of genome of bacteriophage Bac-FRP-5) when the query sequence (i.e., the sequence of genome of bacteriophage Bac-FRP-5) and the target sequence (i.e., the sequence of genome of the previously reported bacteriophage) are analyzed by BLAST alignment analysis. The higher the percent identity is, the more significant the match is. From above definitions for "query cover" and "sequence identity," it will be obvious for the skilled one in the art that the differences of "query cover" and/or "sequence identity" between genomes of two similar bacteriophages make the differences of ORF (open reading frame)'s numbers arranged in the two genomes, then results in the discriminative characteristics (including the range of target strain and strength of antibacterial activity) of two similar bacteriophages.

In this description, the term "Second Bacteriophage" is any bacteriophage that has the ability to specifically kill ETBF and has a genome that has a sequence having less than 90% query cover with at least 90% identity to SEQ ID NO: 1 and has different characteristics from bacteriophage Bac-FRP-5 in terms of the genome topology and the number of ORFs, wherein the genome topology of the Second Bacteriophage is linear form.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing ETBF

Samples were collected from environmental or clinical samples to isolate the bacteriophage capable of killing ETBF. Here, the ETBF strains used for the bacteriophage isolation had been previously isolated and identified as ETBF by the present inventors.

The procedure for isolating the bacteriophage is described in detail hereinafter. The collected sample was added to a BHIB (Brain Heart Infusion Broth) culture medium (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L) inoculated with ETBF at a ratio of 1/100, followed by stationary culture at 37 C for two days under anaerobic condition. Upon completion of the culture, centrifugation was performed at 8,000 rpm for 20 minutes and a supernatant was recovered. The recovered supernatant was inoculated with ETBF at a ratio of 1/100, followed by stationary culture at 37 C for two days under anaerobic condition. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 m filter. The obtained filtrate was used in a typical spot assay for examining whether or not a bacteriophage capable of killing ETBF was included therein.

The spot assay was performed as follows: BHIB culture medium was inoculated with ETBF at a ratio of 1/100, followed by stationary culture at 37° C. for two days under anaerobic condition. 2 ml ($OD_{600}$ of 1.5) of the culture solution of ETBF prepared above was spread on BHIA (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L; agar, 15 g/L) plate. The plate was left on a clean bench for about 30 minutes to dry the spread solution. After drying, 10 l of the prepared filtrate was spotted onto the plate culture medium on which ETBF was spread and then left to dry for about 30 minutes. After drying, the plate culture medium that was subjected to spotting was incubated at 37 C for two days under anaerobic condition, and then examined for the formation of clear zones at the positions where the filtrate was dropped. In the case of the filtrate generated a clear zone, it is judged that the bacteriophage capable of killing ETBF is included therein. Through the above examination, the filtrate containing the bacteriophage having the ability to kill ETBF could be obtained.

The pure bacteriophage was isolated from the filtrate confirmed above to have the bacteriophage capable of killing ETBF. A conventional plaque assay was used to isolate the pure bacteriophage. In detail, a plaque formed in the course of the plaque assay was recovered using a sterilized tip, which was then added to the culture solution of ETBF, followed by culturing at 37 C two days under anaerobic condition. After the culturing, centrifugation was performed at 8,000 rpm for 20 minutes to obtain a supernatant. The ETBF culture solution was added to the obtained supernatant at a volume ratio of 1/50, followed by culturing at 37 C for 2 days under anaerobic condition. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Siphoviridae bacteriophage.

The solution containing the pure bacteriophage confirmed above was subjected to the following purification process. The ETBF culture solution was added to the solution containing the pure bacteriophage at a volume ratio of 1/50 based on the total volume of the bacteriophage solution, followed by further culturing for two days under anaerobic condition. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 m filter, followed by a conventional polyethylene glycol (PEG) precipitation process. Specifically, PEG and NaCl were added to 100 ml of the filtrate until reaching 10% PEG 8000/0.5 M NaCl, and then left at 4 C for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Bac-FRP-5, and then deposited at Korea Collection for Type Culture, Korea Research Institute of Bioscience and Biotechnology on Dec. 9, 2020 (Accession number: KCTC 14403BP).

Example 2: Separation and Sequence Analysis of Genome of Bacteriophage Bac-FRP-5

The genome of the bacteriophage Bac-FRP-5 was separated as follows. The genome was separated from the bacteriophage suspension obtained using the same method as in Example 1. First, in order to remove DNA and RNA of ETBF included in the suspension, 200 U of each of DNase I and RNase A was added to 10 ml of the bacteriophage suspension and then left at 37 C for 30 minutes. After being left for 30 minutes, in order to stop the DNase I and RNase A activity, 500 l of 0.5 M ethylenediaminetetraacetic acid (EDTA) was added thereto and then left for 10 minutes. In addition, the resulting mixture was further left at 65 C for 10 minutes, and 100 l of proteinase K (20 mg/ml) was then added thereto so as to break the outer wall of the bacteriophage, followed by reaction at 37 C for 20 minutes. After that, 500 l of 10% sodium dodecyl sulfate (SDS) was added thereto, followed by reaction at 65 C for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 l of water. This procedure was repeated to obtain a sufficient amount of the genome of the bacteriophage Bac-FRP-5.

Information on the sequence of the genome of the bacteriophage Bac-FRP-5 obtained above was secured by performing next-generation sequencing analysis using Illumina Mi-Seq equipment from the National Instrumentation Center for Environmental Management, Seoul National University. The finally analyzed genome of the bacteriophage Bac-FRP-5 had a size of 46,506 bp, and the sequence of whole genome was expressed by SEQ ID NO: 1.

The homology (similarity) of the bacteriophage Bac-FRP-5 genomic sequence obtained above with previously reported bacteriophage genomic sequences was investigated using BLAST investigation, the genomic sequence of the bacteriophage Bac-FRP-5 was found to have a relatively high homology with the sequence of the *Bacteroides* bacteriophage B40-8 culture-collection ATCC:51477-B1 (Genbank Accession No. FJ008913.1) (query cover: 34%, sequence identity: 87.71%). In addition, the number of open reading frames (ORFs) on the bacteriophage Bac-FRP-5 genome is 64, whereas *Bacteroides* bacteriophage B40-8 culture-collection ATCC:51477-B1 has 46 open reading frames.

Based upon this result, it is concluded that the bacteriophage Bac-FRP-5 must be a novel bacteriophage different from conventionally reported bacteriophages. Further, since the antibacterial strength and spectrum of bacteriophages typically depend on the type of bacteriophage, it is considered that the bacteriophage Bac-FRP-5 can provide antibacterial activity different from that of any other bacteriophages reported previously.

Example 3: Analysis of the Major Structural Proteins of Bacteriophage Bac-FRP-5

Figure 2:
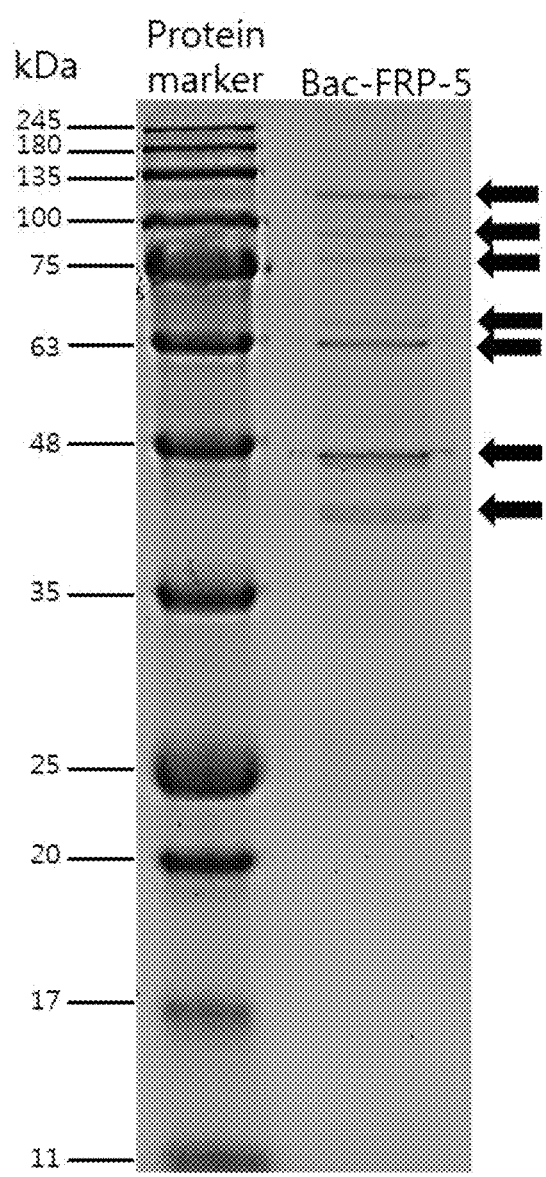
FIG. 2 is a result of the analysis for major structural proteins of bacteriophage Bac-FRP-5.

One-dimensional electrophoresis was performed to analyze the major structural proteins of the bacteriophage Bac-FRP-5. To obtain the proteins constituting the outer wall of the bacteriophage Bac-FRP-5, 200 μl of the bacteriophage suspension prepared in Example 1 was mixed with 800 μl of acetone, which was vortexed vigorously. The mixture stood at −20 C for 10 minutes. Centrifugation was performed at 13,000 rpm at 4 C for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 42 kDa, 48 kDa, 63 kDa, 65 kDa, 75 kDa, 88 kDa, and 118 kDa were confirmed.

Example 4: Investigation of Ability of Bacteriophage Bac-FRP-5 to Kill ETBF

Figure 3:
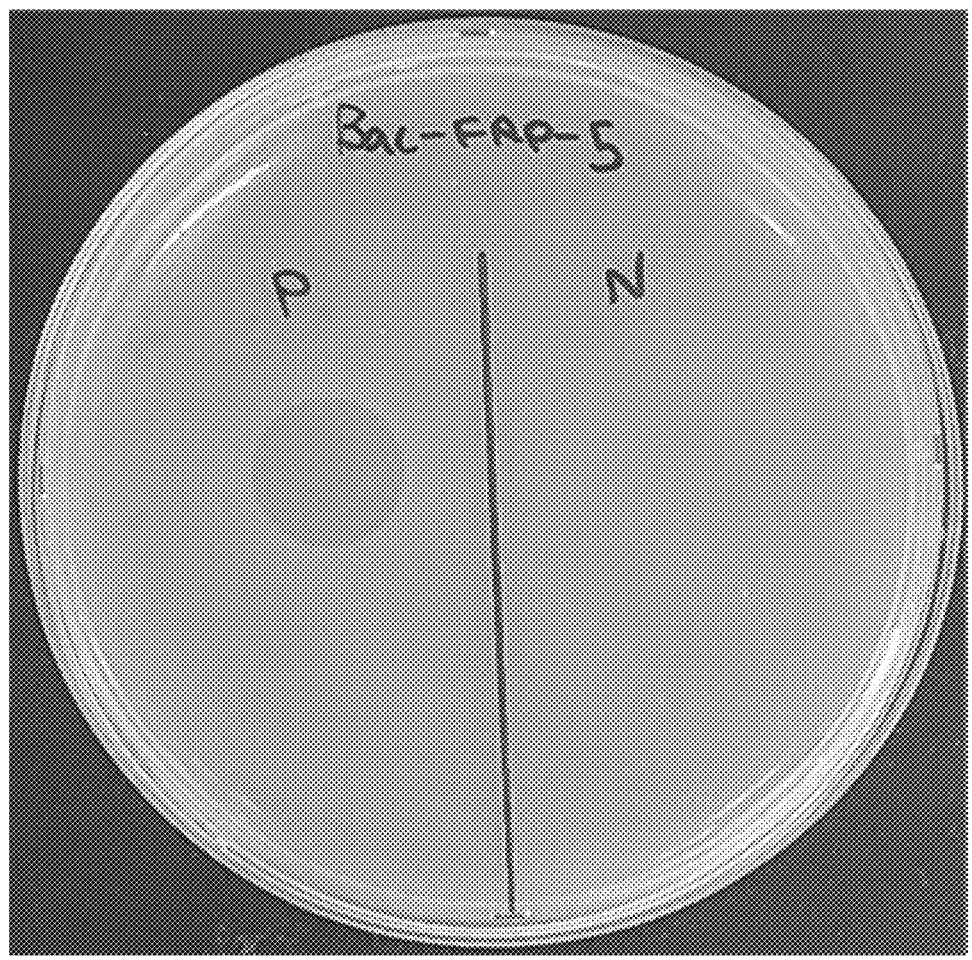
FIG. 3 is a photograph showing the results of an experiment on the ability of the bacteriophage Bac-FRP-5 to kill ETBF. The clear zone is a plaque formed by lysis of the target bacteria.

The ability of bacteriophage Bac-FRP-5 to kill ETBF was investigated. In order to investigate the killing ability, the formation of clear zones was observed using the spot assay in the same manner as described in Example 1. A total of 5 strains that had been identified as ETBF strains were used as ETBF for the investigation of killing ability. The bacteriophage Bac-FRP-5 had the ability to lyse and kill a total of 4 strains among 5 strains of ETBF as the experimental target. The experimental result thereof is presented in Table 1 and the representative result is shown in FIG. 3.

TABLE 1

Test of antibacterial activity of bacteriophage Bac-FRP-5

| Tested ETBF strain | Test result |
|---|---|
| *Bacteroides fragilis* CCARM 18105 | + |
| *Bacteroides fragilis* CCARM 18106 | + |
| *Bacteroides fragilis* CCARM 18107 | − |
| *Bacteroides fragilis* CCARM 18110 | + |
| *Bacteroides fragilis* CCARM 18111 | + |

\* +: clear lytic activity, −: no lytic activity;
CCARM: Culture Collection of Antimicrobial Resistant Microbes (Seoul, Korea)

Meanwhile, the ability of the bacteriophage Bac-FRP-5 to kill *Bordetella bronchiseptica*, *Enterococcus faecalis*, *Enterococcus faecium*, *Staphylococcus aureus*, *Streptococcus pneumonia*, *E. coli* and *Pseudomonas aeruginosa* was also investigated in a separate experiment. As a result, the bacteriophage Bac-FRP-5 did not have the ability to kill these bacteria.

Therefore, it is confirmed that the bacteriophage Bac-FRP-5 has strong ability to kill ETBF and a broad antibacterial spectrum against ETBF, suggesting that the bacteriophage Bac-FRP-5 can be used as an active ingredient of the composition for preventing and treating ETBF infections.

Example 5: Growth Characteristic of Bacteriophage Bac-FRP-5

Figure 4:
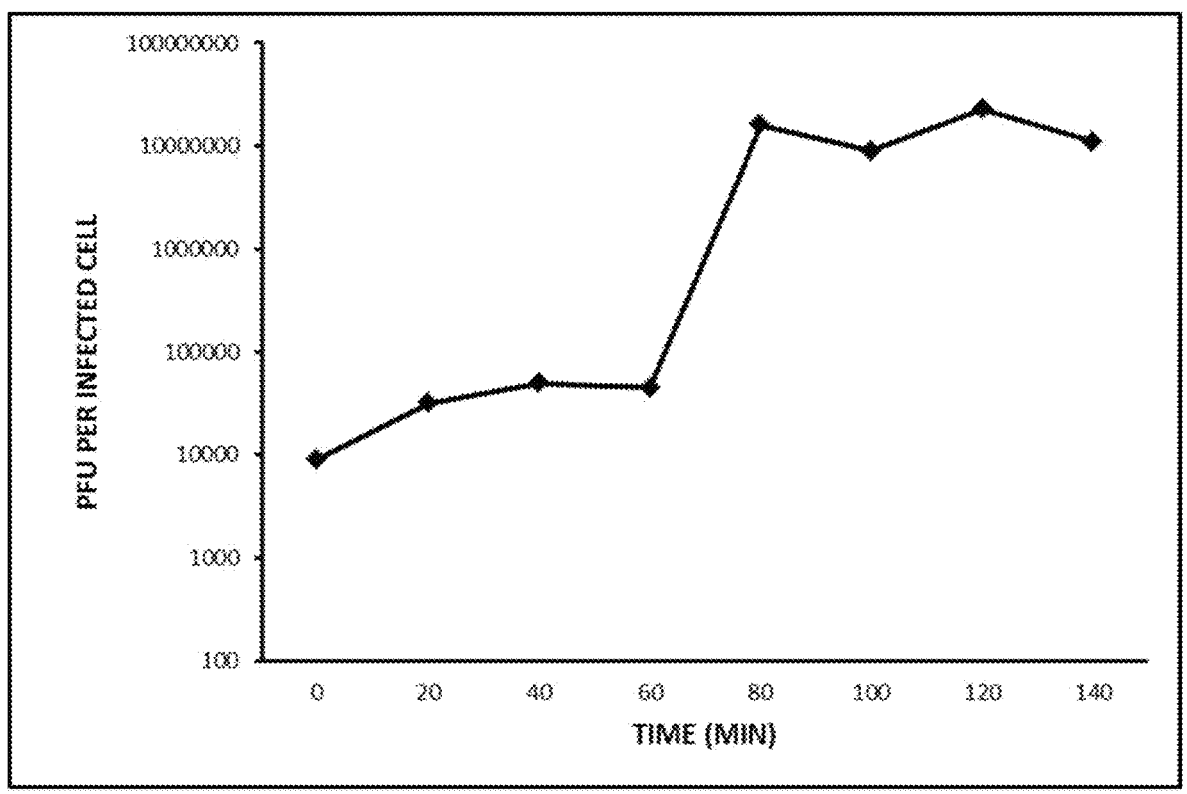
FIG. 4 is the one-step growth curve of bacteriophage Bac-FRP-5.

The growth characteristics of bacteriophage Bac-FRP-5 was analyzed by one-step growth curve analysis. One-step growth curve analysis of bacteriophage Bac-FRP-5 was performed as follows: 50 ml of BHIB (Brain heart infusion broth, Difco) culture medium was inoculated with ETBF at a ratio of 1/100 and followed by stationary culture until exponential phase ($OD_{600}$=0.4-0.5) under anaerobic condition. Upon completion of the culture, centrifugation was performed at 8,000 rpm for 5 min and a bacterial cell pellet was recovered. The recovered pellet was suspended in 50 ml of BHIB. The resulting material may be referred to as a bacterial suspension. The bacteriophage Bac-FRP-5 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of BHIB and incubated at 37 C without shaking. Aliquots were taken at 20 min intervals for 140 min, and the titers in the aliquots were immediately determined by the conventional plaque assay (FIG. 4).

The latent period of bacteriophage Bac-FRP-5 was estimated to be approximately 60±10 min with average burst size of about 320±100 pfu/infected cell.

Example 6: Experimental Example Regarding Prevention of ETBF Infection Using Bacteriophage Bac-FRP-5

100 l of a bacteriophage Bac-FRP-5 suspension ($1\times10^8$ pfu/ml) was added to a tube containing 9 ml of a BHIB culture medium. To another tube containing 9 ml of a BHIB culture medium, only the same amount of BHIB culture medium was further added. A culture solution of ETBF strain (CCARM 18106) was then added to each tube so that absorbance reached about 0.5 at 600 nm. After ETBF was added, the tubes were transferred to an incubator at 37 C, followed by stationary culture, during which the growth of ETBF was observed. As presented in Table 2, it was observed that the growth of ETBF was inhibited in the tube to which the bacteriophage Bac-FRP-5 suspension was added, while the growth of ETBF was not inhibited in the tube to which the bacteriophage suspension was not added.

TABLE 2

Test for bacterial growth inhibition of bacteriophage Bac-FRP-5

| | $OD_{600}$ | | |
| --- | --- | --- | --- |
| Classification | 0 minutes after initiation of cultivation | 120 minutes after initiation of cultivation | 240 minutes after initiation of cultivation |
| Bacteriophage suspension was not added | 0.5 | 0.6 | 0.7 |
| Bacteriophage suspension was added | 0.5 | 0.4 | 0.3 |

The above results indicate that the bacteriophage Bac-FRP-5 of the present invention not only inhibits the growth of ETBF but also has the ability to kill ETBF. Therefore, it is concluded that the bacteriophage Bac-FRP-5 can be used as an active ingredient of the composition for preventing the ETBF infections.

Example 7: Preventive Effect of Bacteriophage Bac-FRP-5 on the Infections of ETBF in Animal Model Preventive effect of the bacteriophage Bac-FRP-5 on weaning pigs affected by ETBF was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the Pt day of the experiment, pigs of the experimental group (adding the bacteriophage) were fed with feeds adding the bacteriophage Bac-FRP-5 at $1\times10^8$ pfu/g according to the conventional feed supply procedure, while pigs of the control group (without adding the bacteriophage) were fed with the same feed without adding the bacteriophage Bac-FRP-5 according to the conventional procedure. From the 7$^{th}$ day of the experiment, the feeds of both groups were contaminated with $1\times10^8$ cfu/g of ETBF for 2 days and thereafter provided twice a day respectively for the experimental and the control groups so as to bring about the infections of ETBF. The administered ETBF suspension was prepared as follows: ETBF strain (CCARM 18110) was anaerobically cultured at 37 C for two days using a BHIB culture medium, after which the bacteria were isolated and adjusted to $10^9$ CFU/ml using physiological saline (pH 7.2). From the next day after providing contaminated feeds for 2 days (the 9$^{th}$ day of the experiment), pigs of the experimental group (adding the bacteriophage) were fed again with the feeds adding the bacteriophage Bac-FRP-5 at $1\times10^8$ pfu/g without contaminating ETBF according to the conventional feed supply procedure as before, while pigs of the control group (without adding the bacteriophage) were fed with the same feed without adding the bacteriophage according to the conventional procedure. From the 9$^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

| | Fecal Consistency score | | | | | |
| --- | --- | --- | --- | --- | --- | --- |
| | D9 | D10 | D11 | D12 | D13 | D14 |
| Control group (bacteriophage suspension was not administered) | 2.25 | 2.0 | 1.75 | 1.5 | 1.25 | 1.0 |
| Experimental group (bacteriophage suspension was administered) | 1.0 | 0.75 | 0.25 | 0.25 | 0 | 0 |

From the above results, it is confirmed that the bacteriophage Bac-FRP-5 of the present invention could be very effective to suppress the infections of ETBF.

Example 8: Example of Treatment of Infectious Diseases of ETBF Using Bacteriophage Bac-FRP-5

The therapeutic effect of the bacteriophage Bac-FRP-5 on diseases caused by ETBF was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of an ETBF suspension was administered to all mice through intraperitoneal injection. The administered ETBF suspension was prepared as follows: ETBF strain (CCARM 18110) was anaerobically cultured at 37 C for two days using a BHIB culture medium, after which the bacteria were isolated and adjusted to $10^9$ CFU/ml using physiological saline (pH 7.2). At 2 hr after administration of ETBF, $10^9$ pfu of bacteriophage Bac-FRP-5 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of ETBF until the end of the test. The results are shown in Table 4 below.

TABLE 4

| | Survival rate (%) | | | | | |
|---|---|---|---|---|---|---|
| | D2 | D3 | D4 | D5 | D6 | D7 |
| Control group (not administered with bacteriophage suspension) | 100 | 80 | 50 | 45 | 20 | 15 |
| Experimental group (administered with bacteriophage suspension through intraperitoneal injection) | 100 | 85 | 85 | 80 | 80 | 80 |

As is apparent from the above results, it can be concluded that the bacteriophage Bac-FRP-5 of the present invention is very effective in the treatment of diseases caused by ETBF.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number

Name of Depositary Authority: Korean Collection for Type Cultures (KCTC), Korea Research Institute of Bioscience and Biotechnology, 181 Ipsin-gil. Jeongeup-si, Jeollabuk-do 56212, Republic of Korea
Accession number: KCTC 14403BP
Accession date: Dec. 9, 2020

What is claimed is:

1. A method for preventing or treating an infection or disease caused by enterotoxigenic *Bacteroides fragilis* comprising:

administering to a subject a composition containing Siphoviridae bacteriophage Bac-FRP-5 and a pharmaceutically acceptable carrier, wherein the Siphoviridae bacteriophage Bac-FRP-5 is deposited in the Korean Collection for Type Culture (KCTC) under accession number KCTC 14403BP and has an ability to lyse the enterotoxigenic *Bacteroides fragilis* cells and the genome sequence as set forth in SEQ ID NO: 1, wherein the Siphoviridae bacteriophage Bac-FRP-5 has a latent period of 10-100 minutes and a burst size of 150-540 plaque-forming units (PFU)/infected cell, wherein the Siphoviridae bacteriophage Bac-FRP-5 has structural proteins in the size of approximately 42 kDa, 48 kDa, 63 kDa, 65 kDa, 75 kDa, 88 kDa, and 118 kDa; and wherein the composition has a concentration of Siphoviridae bacteriophage Bac-FRP-5 of $1\times10^4$ pfu/ml to $1\times10^{15}$ pfu/ml or $1\times10^4$ pfu/g to $1\times10^{15}$ pfu/g.

2. The method of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, methylcellulose, methylhydroxybenzoate, propylhydroxybenzoate, talc, magnesium stearate, or mineral oil.

3. The method of claim 1, wherein the composition further contains one or more selected from the group consisting of a lubricant, a wetting agent, a sweetener, a flavor, an emulsifier, a suspending agent, and a preservative.

4. The method of claim 1, wherein the infection or disease is acute or chronic intestinal disease, selected from the group consisting of diarrhea, colitis and colonic neoplasia, bacteremia, and colorectal cancer.

5. The method of claim 1, wherein the composition is a solution, suspension, emulsion in oil, water-soluble medium, extract, powder, granule, tablet, or capsule.

* * * * *